United States Patent [19]
Arakaki et al.

[11] Patent Number: 5,931,779
[45] Date of Patent: Aug. 3, 1999

[54] REAL-TIME IN-VIVO MEASUREMENT OF MYOGLOBIN OXYGEN SATURATION

[75] Inventors: Lorilee S. Arakaki, Narberth, Pa.; Eric Feigl, Seattle, Wash.; Martin J. Kushmerick, Seattle, Wash.; David Marble, Seattle, Wash.; David H. Burns, Montreal, Canada; Kenneth H. Schenkman, Madison, Wis.

[73] Assignee: Wisconsin Alumni Research Foundation, Madison, Wis.

[21] Appl. No.: 08/870,483

[22] Filed: Jun. 6, 1997

Related U.S. Application Data

[60] Provisional application No. 60/019,215, Jun. 6, 1996.

[51] Int. Cl.$^6$ ........................................................ A61B 5/00
[52] U.S. Cl. .......................... 600/310; 600/473; 600/476
[58] Field of Search ................................... 600/310, 311, 600/323, 328, 340, 342, 473, 476

[56] References Cited

U.S. PATENT DOCUMENTS

| | | | |
|---|---|---|---|
| 5,190,039 | 3/1993 | Takeuchi et al. | 600/323 |
| 5,231,464 | 7/1993 | Ichimura et al. | 600/310 |
| 5,517,987 | 5/1996 | Tsuchiya | 600/328 |

OTHER PUBLICATIONS

Aldridge, P.K. et al. (1994), "Identification of Tablet Formulations Inside Blister Packages by Near–Infrared Spectroscopy," Appl. Spectrosc. 48(10):1272–1276.

Anthony, A. et al. (1959), "Effects of altitude acclimatization on rat myoglobin. Changes in myoglobin content of skeletal and cardiac muscle," Am. J. Physiol. 196:512–516.

Antonini, E. and Brunori, M. (1971), *Hemoglobin and Myoglobin in Their Reactions with Ligands*, North–Holland Publishing Co., Amsterdam, pp. 19–20.

Arakaki, L.S.L. (1995), "An Optical Method for Myoglobin Oxygenenation Measurements in the Blood–Perfused Rat Hind Limb," Doctoral Dissertation, University of Washington, Seattle.

Arakaki, L.S.L. and Burns, D.H. (1992), "Multispectral Analysis for Quantitative Measurements of Myoglobin Oxygen Fractional Saturation in the Presence of Hemoglobin Interference," Appl. Spectrosc. 46(12):1919–1928.

Beebe, K.R. and Kowalski, B.R. (1987), "An Introduction to Multivariate Calibration and Analysis," Anal. Chem. 59(17):1007A–1017A.

Caspary, L. et al. (1985), "Multicomponent analysis of reflection spectra from the guinea pig heart for measuring tissue oxygenation by quantitative determination of oxygen saturation of myoglobin and of the redox state of cytochrome aa$_3$, c, and b," Adv. Exp. Med. Biol. 191:263–270.

Cheong, W.F. et al. (1990), "A Review of the Optical Properties of Biological Tissues," IEEE J. Quant. Elec. 26(12):2166–2185.

Cleman, M. et al. (1986), "Prevention of ischemia during percutaneous transluminal coronary angioplasty by transcatheter infusion of oxygenated 'Fluosol' DA 20%," Circulation 74(3):555–562.

Cope, M. et al. (1991), "Data analysis methods for near infrared spectroscopy of tissue: problems in determining the relative cytochrome aa$_3$ concentration," SPIE 1431:251–262.

Cui, W. et al. (1991), "Experimental Study of Migration Depth for the Photons Measured at Sample Surface," SPIE 1431:180–191.

(List continued on next page.)

*Primary Examiner*—Cary E. O'Connor
*Assistant Examiner*—Eric F. Winakur
*Attorney, Agent, or Firm*—Greenlee, Winner & Sullivan, P.C.

[57] ABSTRACT

A method for determining myoglobin oxygen fractional saturation in vivo in muscle tissue and intracellular oxygen tension (pO$_2$), typically in the presence of hemoglobin, is provided. The method comprises measuring the absorption spectrum of the tissue using spectrographic equipment known to the art, including equipment for non-invasively taking spectroscopic measurements of tissue, or adaptations of such equipment to provide the preferred measurements described herein, or using spectrographic equipment specifically designed as described herein for use in non-invasive measurements of reflectance spectra. The measured spectrum is corrected for light scattering effects, such as by taking the second derivative of the data, or by using other means which are known to the art. Myoglobin fractional oxygen saturation is calculated from the measured spectrum employing calibration coefficients that are themselves calculated from application of multivariate analysis to a calibration set created from the second derivatives of absorption spectra. The calibration set spectra preferably representing absorbances of (1) a range of concentrations of hemoglobin (wherein a range of concentrations of oxyhemoglobin and deoxyhemoglobin are present), (2) one concentration of myoglobin (preferably selected to match the concentration of myoglobin in the target muscle tissue) with varying relative amounts of oxy- and deoxymyoglobin and (3) a range of concentrations of scattering agents to mimic scattering encountered in target tissue. The range of concentrations of oxy- and deoxyhemoglobin and the relative amounts of oxy- and deoxymyoglobin represented in calibration set spectra span the range of concentrations of these species encountered in the target tissue. Sample tissue spectra are preferably measured in the visible, the near-infrared or both wavelength ranges. Diffuse reflectance spectroscopy is the preferred method for obtaining spectral data. A partial least squares (PLS) method is preferably used to calculate calibration coefficients from the calibration set which in turn are used to calculate myoglobin oxygen saturation from the measured data. Other means known to the art may also be used. Measured myoglobin oxygen saturation determinations can be used to calculate intracellular oxygen tension, if accurate p50 values at appropriate physiologic pH and temperature for myoglobin-oxygen dissociation are available. An improved method of accurate determination of myoglobin-oxygen dissociation curves under physiologically relevant conditions is also provided.

24 Claims, 12 Drawing Sheets

OTHER PUBLICATIONS

Drabkin, D.L. (1950), "The Distribution of the Chromoproteins, Hemoglobin, Myoglovin, and Cytochrome c, in the Tissues of Different Species, and the Relationship of the Total Content of Each Chromoprotein to Body Mass," J. Biol. Chem. 182:317–333.

Elwell, C.E. et al. (1994), "Quantification of adult cerebral hemodynamics by near–infrared spectroscopy," J. Appl. Physiol. 77:2753–2760.

Feigl, E.O. (1983), "Coronary Physiology," Physiol. Rev. 63:1–205.

Flock, S.T. et al. (1989), "Monte Carlo Modeling of Light Propagation in Highly Scattering Tissues—I: Model Predictions and Comparison with Diffusion Theory," IEEE Trans. Biomed. Eng. 36(12):1162–1167.

Gayeski, T.E.J. et al. (1985), "Oxygen transport in rest–work transition illustrates new functions for myoglobin," Am. J. Physiol. 248:H914–H921.

Gayeski, T.E.J. Honig, C.R. (1991), "Intracellular $PO_2$ in individual cardiac myocytes in dogs, cats, rabbits, ferrets, and rats," 260:H522–H531.

Greeley, W.J. et al. (1991), "Recovery of Cerebral Metabolism and Mitochondrial Oxidation State is Delayed After Hypothermic Circulatory Arrest," Circulation 84(5):400–406.

Haaland, D.M. and Thomas, E.V. (1988), "Partial Least–Squares Methods for Spectral Analyses. 1. Relation to Other Quantitative Calibration Methods and the Extraction of Qualitative Information," Anal. Chem. 60:1193–1202.

Harms, S.J. and Hickson, R.C. (1983), "Skeletal muscle mitochondria and myoglobin, endurance, and intensity of training," J. Appl. Physiol.: Respirat. Environ. Exercise Physiol. 54:798–802.

Hoffman, J. and Lübbers, D.W. (1986), "Estimation of concentration Ratios and the Redox States of the Cytochromes From Noisy Reflection Spectra Using Multicomponent Analysis Methods," Adv. Exp. Med. Biol. 200:119–124.

Hoffman, J. and Lübbers, D.W. (1986), "Improved Quantitative Analysis of Reflection Spectra Obtained from the Surface of the Isolated Perfused Guinea Pig Heart," Adv. Exp. Med. Biol. 200:125–130.

Hoffmann, J. et al. (1984), "Analysis of Tissue Reflection Spectra Obtained from Brain or Heart, Using the Two Flux Theory for Non–Constant Light Scattering," Adv. Exp. Med. Biol. 180:555–563.

Hoffmann, J. et al. (1985), "Simulation of the Optical Properties of an Absorbing and Scattering Medium Using the Monte–Carlo Technique Compared with Two– and Six––Flux Theroies," Adv. Exp. Med. Biol. 191:883–888.

Holler, F. et al. (1989), "Direct Use of Second Derivatives in Curve–Fitting Procedures," Appl. Spectrosc. 43(5):877–882.

Kagen, L.J. (1973), in *Myoglobin, Biochemical, Physiological, and Clinical Aspects. 2. Chemical Factors*, Columbia University Press, New York and London, pp. 9–13.

Lorber, A. et al. (1987), "A Theoretical Foundation for the PLS Algorithm," J. Chemom. 1:19–31.

Marble, D.M. et al. (1994), "Diffusion–based model of pulse oximetry: in vitro and in vivo comparison," Appl. Opt. 33(7):1279–1285.

Mark, H.L. and Tunnell, D. (1985), "Qualitative Near–Infrared Refelctance Analysis Using Mahalanobis Distances," Anal. Chem. 57:1449–1456.

Martens, H. et al. (1987), Improved Selectivity in Spectroscopy by Multivariate Calibration, J. Chemom. 1:201–219.

Meng, H. et al. (1993), "Myoglobin content of hamster skeletal muscles," J. Appl. Physiol. 74:2194–2197.

Mohrman, D.E. and Feigl, E.O. (1978), "Competition between sympathetic vasoconstriction and metabolic vasodilation in the canine coronary circulation," Circ. Res. 42:79–86.

Oshino, R. et al. (1972), "A Sensitive Bacgerial Luminescence Probe for $O_2$ in Biochemical Systems," Biochem. Biophys. Acta 273:5–17.

Parsons, W.J. et al. (1993), "Myocardial Oxygenation in Dogs During Partial and Complete Coronary Artery Occlusion," Circ. Res. 73(3):458–464.

Parsons, W.J. et al. (1990), "Dynamic mechanisms of cardiac oxygenation during brief ischemia and reperfusion," Am. J. Physiol. 259(5pt2):H1477–H1485.

Ross, P.D. and Warme, P.K. (1977), "Myoglobin as an Oxygen Indicator for Measuring the Oxygen Binding Characteristics of a Modified Myoglobin Derivative Containing Covalently Bound Mesoheme," Biochemistry 16:2560–2565.

Schenkman, K.A. and Burns, D.H. (1994), "Measurement of myoglobin oxygen saturation in the presence of hemoglobin interference by near–infrared spectroscopy," SPIE 2131:468–474.

Schenkman, K.A. et al. (1997), "Myoglobin oxygen dissociation by multiwavelength spectroscopy," J. Appl. Physiol. 82(1):86–92.

Severinghaus (1993), "History and recent development in pulse oximetry," Scand. J. Clin. Lab. Invest., Suppl. 214:105–111.

Shah, N.K. and Gemperline, P.J. (1989), "A program for calculating Mahalanobis distances using principal component analysis," Trends Anal. Chem. 8(10):357–361.

Skov, L. et al. (1993), "Estimation of Cerebral Venous Saturation in Newborn Infants by Near Infrared Spectroscopy," Ped. Res. 33(1):52–55.

Tamura, M. et al. (1989), "In Vivo Study of Tissue Oxygen Metabolism Using Optical and Nuclear Magnetic Resonance Spectroscopies," Annu. Rev. Physiol. 51:813–834.

Tamura, M. et al. (1983), "Heme–Modification Studies of Myoglobin. II. Ligand Binding Characteristics of Ferric and Ferrous Myoglobins Containing Unnatural Hemes," Biochem. Biophys. Acta 317:34–49.

Tamura, M. et al. (1978), "Optical Measurements of Intracellular Oxygen Concentration of Rat Heart In Vitro," Arch. Biochem. Biophys. 191(1):8–22.

Thorniley, M.S. et al. (1996), "Non–invasive measurement of caridac oxygenation and haemodynamics during transient episodes of coronary artery occlusion and reperfusion in the pig," Clin. Sci. 91:51–58.

Vanderkooi, J.M. et al. (1991), "Oxygen in mammalian tissue: methods of measurement and affinities of various reactions," Am. J. Physiol. 260(29):C1131–1150.

Whitfield, R.G. et al. (1987), "Near–Infrared Spectrum Qualification via Mahalanobis Distance Determination," Appl. Spectrosc. 41(7):1204–1213.

Wittenberg, B.A. and Wittenberg, J.B. (1989), "Transport of Oxygen in Muscle," Annu. Rev. Physiol. 51:857–878.

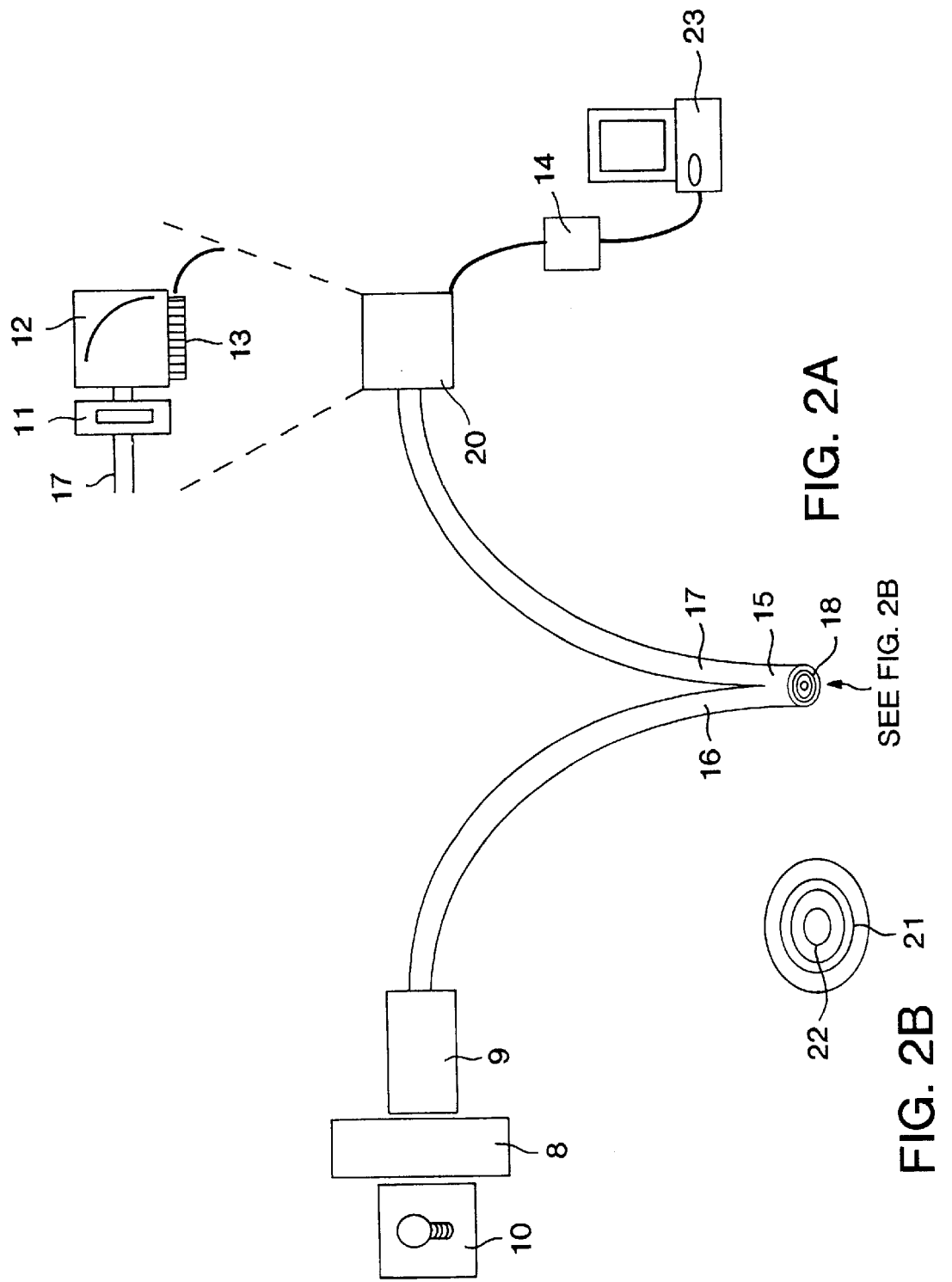

REAL-TIME IN-VIVO MEASUREMENT OF MYOGLOBIN OXYGEN SATURATION

CROSS-REFERENCE TO RELATED APPLICATIONS

This application takes priority under 35 U.S.C. § 119(e) from U.S. provisional application Ser. No. 60/019,215, filed Jun. 6, 1996 which is incorporated in its entirety by reference herein.

This invention was made at least in part through funding from the United States government through National Institute of Health Grants: RO1 HL49228, RO1 HL49822, and AR36281; and NSERC 06PO155504. The United States government has certain rights in this invention.

BACKGROUND OF THE INVENTION

The ability to determined intracellular oxygenation in muscle is useful in physiology and pathology, and in applied clinical areas such as cardiac surgery, e.g., during by-pass surgery, and sports medicine. Application of such measurements to the study of the control of oxidative metabolism in the muscle cell is of particular interest. The availability of in-vivo, real-time measurements of cardiac muscle oxidation, for example during surgery to assess reperfusion treatment, provides means for improved control and monitoring of medical and surgical procedures. The cause and effect relationships between the amount of work a muscle does, levels of metabolites (e.g., intracellular oxygen, NADH, and ADP), and physiological responses (blood flow and oxygen consumption) are not fully understood. This results, at least in part, because the majority of studies on intracellular oxygenation to date have been done in vitro, on single cells, or on ex vivo preparations. A systems perspective is thus needed to better understand and analyze the performance of a muscle in its normal, blood-perfused state. A non-invasive measurement of myoglobin saturation and intracellular oxygen tension in vivo represents a significant advance toward these goals.

Myoglobin is found in skeletal and cardiac muscle, and is an endogenous marker for oxygen tension. The absorbance spectrum of myoglobin is a function of oxygen binding, and differences in the oxygenated and deoxygenated state of the molecule can be measured in both the visible and near-infrared spectral regions. Myoglobin oxygenation is quantified by S, the fractional saturation, which is defined as:

$$S=[MbO_2]/([MbO_2]+[Mb]), \quad (1)$$

where $[MbO_2]$ is the concentration of oxymyoglobin and $[Mb]$ is the concentration of deoxymyoglobin. Because each myoglobin molecule binds a single molecule of oxygen, an equivalent definition for fractional saturation is the ratio between the mole fractions of myoglobin molecules bound to oxygen, $[MbO_2]$, and the total number of myoglobin molecules present, $[MbO_2]+[Mb]$.

Myoglobin fractional saturation is related to the partial pressure of oxygen ($pO_2$) in a cell by the myoglobin oxygen dissociation curves. These curves describe the amount of oxygen bound to myoglobin at different temperatures and oxygen tensions. The single oxygen binding site of myoglobin dictates a hyperbolic shape for the curves according to the equation:

$$S=pO_2/(pO_2+p50), \quad (2A)$$

where $pO_2$ is the partial pressure of oxygen dissolved in the myoglobin solution and p50 is the $pO_2$ value associated with a myoglobin S of 0.5. Once myoglobin fractional saturation is measured, intracellular $pO_2$ values can be obtained through inversion of equation 2A:

$$S \times p50/(1-S)=pO_2, \quad (2B)$$

if accurate p50 values are known for the appropriate physiological conditions (pH, temperature, etc.).

Over the past two decades there has been significant interest in using spectroscopic techniques to make non-invasive measurements of metabolic conditions. Pulse-oximetry provides real-time, non-invasive measurement of arterial blood oxygen saturation (J. Severinghaus, "History and recent development in pulse oximetry," (1993) *Scand. J. Clin. Lab. Invest.*, Suppl. 214: 105–111.) Optical spectroscopy has been used for real-time measurements of cytochrome oxidative states in brain tissue (W. J. Greeley, et al. "Recovery of cerebral metabolism and mitochondrial oxidation state is delayed after hypothermic circulatory arrest," (1991) *Circulation* 84:400–406), as well as for hemoglobin saturation and blood flow measurements (C. E. Elwell et al. (1994) "Quantification of adult cerebral hemodynamics by near-infrared spectroscopy," *J. Appl. Physiol.* 77:2753–2760; and L. Skov et al. (1993) "Estimation of cerebral venous saturation in newborn infants by near-infrared spectroscopy," *Pediatr. Res.*, 33:52–55.)

The primary problem with quantifying myoglobin saturation using optical spectroscopy in vivo has been that myoglobin and hemoglobin have very similar absorbance properties, as shown in the original measurements by Millikan, G. A. (1939) *Physiol. Rev.* 19:503 and as illustrated in FIGS. 1A and 1B. FIG. 1A is a plot of the visible and near-infrared spectra of hemoglobin and myoglobin in the oxygenated and deoxygenated states. FIG. 1B is an expanded scale plot of the spectra of FIG. 1A in the near-infrared region. The spectral overlap between the two proteins is very large, making the differentiation between myoglobin and hemoglobin spectra difficult. It has generally been concluded in the art that the optical absorbance characteristics of hemoglobin and myoglobin are too similar to allow for independent measurement of intracellular oxygen saturation of myoglobin in living, blood-perfused tissue (Tamura, M. and O. Hazeki (1989) "In vivo study of tissue oxygen metabolism using optical and nuclear magnetic resonance spectroscopies," *Annu. Rev. Physiol.* 51.:813–834; Vanderkooi, J. M., et al. (1991) "Oxygen in mammalian tissue: methods of measurement and affinities of various reactions," *Am. J. Physiol.*, 260(29): C1131–C1150). Previous measurements from the beating heart have combined myoglobin and hemoglobin saturation (W. J. Parsons, et al. (1990) "Dynamic mechanisms of cardiac oxygenation during brief ischemia and reperfusion," *Am. J. Physiol.*, 259 (5pt2) H1477–1485; W. J. Parsons et al. (1993) "Myocardial oxygenation in dogs during partial and complete coronary artery condition," *Circ. Res.*, 73:458–464). A recent report of a method for non-invasive measurement of cardiac oxygenation and hemodynamics (Thorniley, M. S. et al. (1996) "Non-invasive measurement of cardiac oxygenation and haemodynamics during transient episodes of coronary artery occlusion and reperfusion in the pig," *Clinical Science*, 91:51–58), which employed near-infrared spectroscopy to measure changes in hemoglobin oxygen saturation to assess myocardial oxygenation, did not separately determine myoglobin oxygen saturation from that of hemoglobin.

Successful myoglobin saturation measurements in tissue have only been made with hemoglobin-free preparations (Tamura, M. et al. (1978) Arch. Biochem. Biophys. 191:8;

Caspary, L. et al. (1985) Adv. Exp. Med. Biol. 191:263; Hoffmann, J. and Lubbers, D. W. (1986) Adv. Exp. Med. Biol. 200:125) or using cryomicrospectroscopy (Gayeski, T. E. and Honig, C. R. (1991) Am. J. Physiol. 260:H522), wherein muscle cells can be examined separately from erythrocytes. Unfortunately, this latter method cannot provide in vivo measurements of myoglobin saturation from a muscle, since the tissue is excised before spectral examination.

Chemometrics provides methods for analyzing large matrices of data to identify relationships between an analyte concentration and a complex data set which represents the sample of interest. (M. A. Sharaf et al. (1986) *Chemometrics*, New York , Wiley).

The methods of chemometrics, multivariate analysis, such as the partial least squares analysis, have been particularly useful in analyzing multiwavelength spectral data sets to determine concentrations of single analytes in the complex system.

Multilinear regression and second-derivative preprocessing allow myoglobin fractional saturation to be determined from spectra that contain both myoglobin and hemoglobin in vitro in the visible (Arakaki, L. S. L. and Burns, D. H. (1992) Appl. Spectrosc. 46:1919) as well as in the near-infrared spectral regions (Schenkman, K. A. and Burns, D. H. (1994) "Measurement of myoglobin oxygen saturation in the presence of hemoglobin interference by near-infrared spectroscopy," *Proc. SPIE*, 2131:468). The solutions examined in these experiments, however, did not contain scattering species. Since muscle tissue is a turbid medium with high scattering coefficients, the effects of scattering on myoglobin oxygenation measurements in vivo must be determined to obtain accurate results.

SUMMARY OF THE INVENTION

This invention provides an optical method for real-time, non-invasive clinical measurement of muscle tissue oxygen saturation. The method most generally involves the in vivo measurement of an absorbance spectrum of muscle tissue and the application of multivariate analysis to calculate myoglobin oxygen saturation of that tissue. More specifically, the invention provides a method for independent measurement of intracellular oxygen saturation of myoglobin in blood-perfused tissue, particularly in living, blood-perfused tissue. The method allows measurement of myoglobin oxygen saturation independent of the presence of hemoglobin species. In a specific embodiment, the method employs diffuse reflectance optical spectroscopy to non-invasively measure absorbances in tissue. In a preferred method, sample spectra of tissue and the spectra of a calibration set are measured in the visible and/or near-infrared spectral regions. The method allows real-time, continuous measurement of myoglobin saturation and with accurate data on myoglobin-oxygen dissociation under physiologically relevant pH and temperature conditions also allows real-time, continuous measurement of intracellular oxygen tension.

The method of this invention for measurement of myoglobin oxygen saturation involves the general steps of:

(a) measuring an absorption spectrum of muscle tissue in vivo, and (b) calculating the myoglobin fractional oxygen saturation from the measured absorption data using calibration coefficients determined from multivariate analysis employing a calibration set comprising in vitro absorbance spectra.

A calibration set of spectra appropriate for the type of muscle tissue being examined is typically developed and calibration coefficients are calculated using multivariate analysis from that calibration set prior to the measurement of in vivo tissue samples. Myoglobin oxygen saturation for a given measured tissue spectrum is calculated by a linear summing of the products of the spectral absorbance at a given wavelength and the calibration coefficient at that wavelength over the wavelength region of interest.

The method of this invention for determination of intracellular oxygen tension involves the steps of:

(a) measuring myoglobin fractional oxygen saturation in vivo in muscle tissue as described above, and (b) calculating the intracellular oxygen tension of that muscle tissue from the oxygen saturation data of step(a) employing a p50 value obtained from an optical spectroscopic determination of myoglobin-oxygen dissociation curves.

The measured absorption spectra are preferably mathematically manipulated after accumulation to compensate for the effect of variation in scattering coefficients, to compensate for the effect of the use of summed spectra in the calibration set and/or to enhance the difference between absorbing species. The spectra can be manipulated by any means known in the art to achieve these desired results. In particular, a spectrum can be subjected to a smoothing function, it can be normalized, or a mathematical derivative of each spectrum can be taken.

The spectra of the calibration set are preferably subjected to the some mathematically treatment as the measure spectrum.

In the methods of this invention it is preferred that the second-derivatives of the measured spectrum be employed and that the calibration set comprises second-derivatives of absorbance spectra.

In a specific embodiment, this invention describes an improved method for determination of myoglobin-oxygen dissociation curves under physiologically relevant conditions and which compensates for the presence of metmyoglobin. Dissociation curve data determined by this improved method when combined with the myoglobin oxygen saturation of this invention allows the determination of intracellular oxygen tension with increased accuracy.

A statistical multivariate analysis method is used to calculate myoglobin oxygen saturation from sample optical spectra of blood-perfused tissue containing both myoglobin and hemoglobin absorbances. The preferred method of statistical analysis applied to the measured sample spectra is a partial least squares analysis (PLS). PLS employs a calibration set of optical spectra, obtained in vitro, of representative samples prepared to simulate the absorbances expected in in vivo tissue samples, containing absorbances of the major absorbing species in the tissue and spanning the range of concentration of those absorbing species expected to be encountered in the tissue samples.

Calibration set samples contain a constant total myoglobin concentration selected to be approximately the same as that expected in the target muscle tissue. The relative amounts of oxy- and deoxymyoglobin is varied among the calibration set samples.

Calibration set samples also contain varying amounts of total hemoglobin, as well as variations in the relative amounts of oxy- and deoxyhemoglobin. Calibration set samples also contains varying amounts of light scattering agent that mimics scattering observed in tissue absorbance measurements. The calibration set is constructed to contain representative spectra in which myoglobin and hemoglobin oxygen saturation can be varied independently of one another. These spectra are obtained by mathematical summing of spectra obtained from separate solutions containing either myoglobin or hemoglobin. Independent variation of myoglobin and hemoglobin oxygen saturation can not be achieved in solutions containing both components. Calibration samples can be prepared using hemoglobin and/or myoglobin from any mammalian source.

In a specific embodiment, second derivatives of optical spectra were employed both to create the calibration set and in tissue sample measurement. Second derivative spectra were employed to decrease the error due to scattering variations and also to decrease any error due to the use of summed spectra in the calibration set.

The method of the present invention can in general be applied to spectral absorbance of muscle tissue in any wavelength region in which there is sufficient difference in myoglobin and hemoglobin absorbances to allow the species to be distinguished. The method is applied specifically to optical transmission or reflectance spectroscopy in the visible wavelength region or the near infra-red wavelength region. The preferred method of this invention employs optical reflectance spectroscopy in the visible, the near-infrared or both.

This invention also provides a fiber optic probe device for real-time, non-invasive measurement of intracellular myoglobin oxygen saturation levels and/or intracellular oxygen tension in muscle tissue, i.e., a cellular oximeter. The device allows collection of reflectance spectra from exposed muscle in vivo without damage to the muscle tissue. Spectral data collected employing the fiber optic probe device are subjected to multivariate analysis as described herein above to determine the desired values.

The method of the present invention can be applied to in vivo absorption spectra of tissue measured over time to follow relative changes in myoglobin oxygen saturation and/or intracellular oxygen tension. Relative myoglobin oxygen saturation values determined by this method can be scaled to upper and lower limits of myoglobin oxygen saturation by a variety of methods to give absolute values to facilitate comparisons, for example between determinations from different muscle tissues, different patients or from the same patient at different times. Relative myoglobin oxygen saturation values can also be normalized to a selected standard value, e.g. that of an average healthy adult.

BRIEF DESCRIPTION OF THE DRAWINGS

FIG. 2 is a schematic drawing of a device for non-invasive measurement of myoglobin oxygen saturation and/or intracellular oxygen tension including a view of one arrangement of fibers at the distal end of the fiber optic probe.

Inclusion of shorter wavelengths was not possible due to decreasing signal to noise ratio in the visible region. Negative correlation is seen around 745 nm due to the negative second derivative peak from myoglobin.

Figure 13:
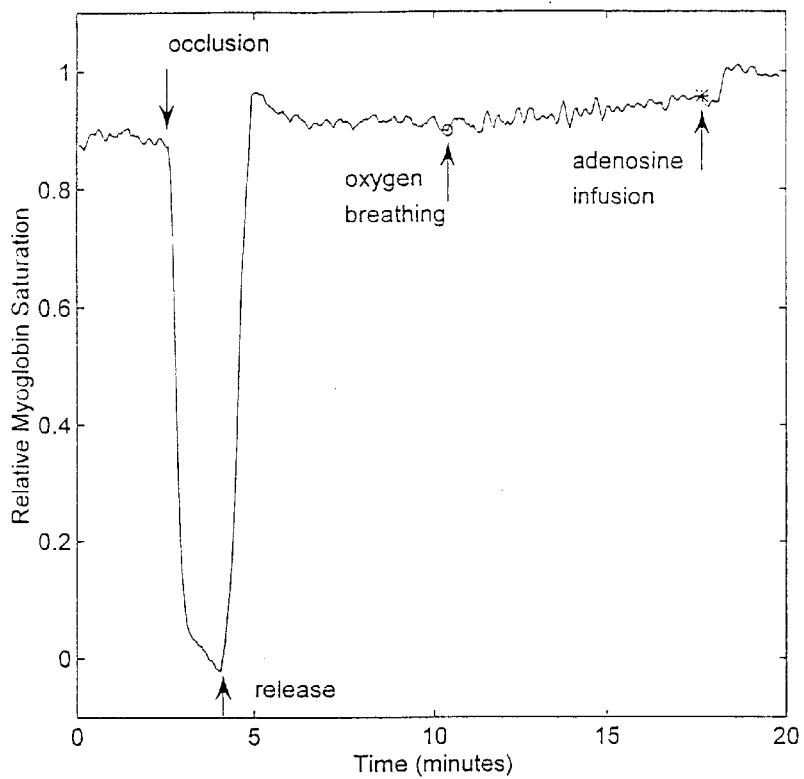

FIG. 13 illustrates results from a coronary occlusion experiment. The rapid decrease in saturation upon occlusion of the coronary, as well as the rapid resaturation upon release, can be seen. In addition, saturation occurs within about 1 minute following release. The change in saturation upon administration of oxygen (shown in open circle) appears to occur slowly over about 4 minutes as the lung washout of nitrogen occurs. Following the initiation of intracoronary adenosine infusion (marked by the *), there is a rapid rise in myoglobin saturation.

Figure 14:
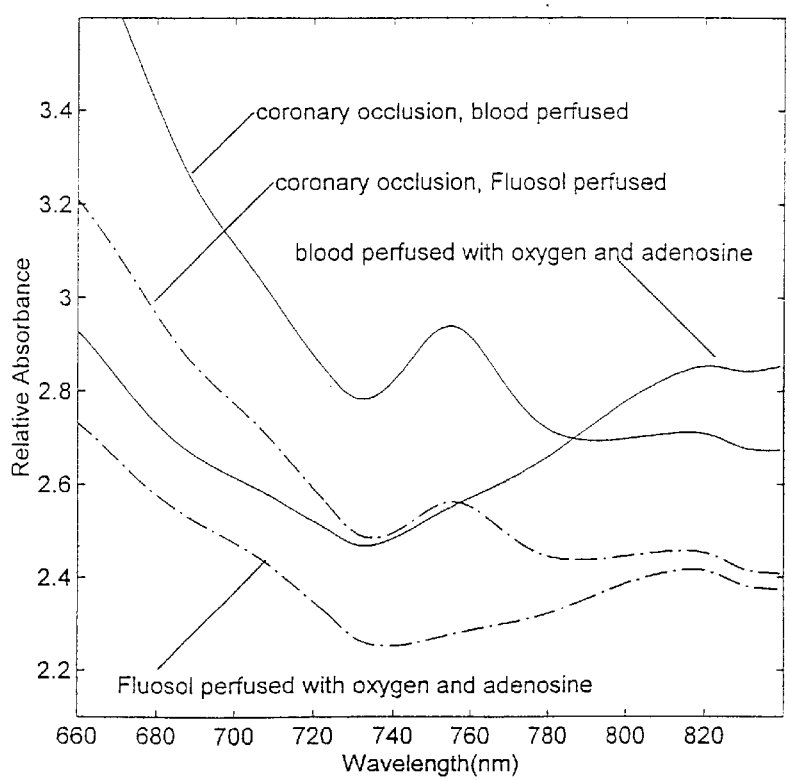

FIG. 14 provides the unprocessed spectra for blood- and "Fluosol" (Alpha Therapeutics)-perfused heart under oxygenated and deoxygenated conditions. There is significant decrease in overall absorbance for the spectra from the "Fluosol"-perfused heart. There is a slight rightward shift of the deoxygenated spectrum from the "Fluosol"-perfused heart relative to the blood-perfused heart. The decrease in absorbance is due to the absence of hemoglobin in the "Fluosol" perfusion.

DETAILED DESCRIPTION OF THE INVENTION

FIG. 2 illustrates a fiber optic probe system (not drawn to scale) for non-invasive measurement of myoglobin saturation and intracellular oxygen tension in muscle tissue in vivo.

The system contains a fiber-optic spectrophotometer with a fiber-optic reflectance probe. The system includes a light source (10), a fiber-optic probe (15) optically coupled to the light source and to a detector (20), for example a detector comprising a spectrograph and photodiode array. The probe is a bifurcated fiber optic having an input fiber optic bundle (16, the illuminating fibers) and an output fiber optic bundle (17, the detector fibers). Each fiber bundle contains a plurality of optically conductive fibers (preferably glass fibers). At the distal end of the probe (18), the two fiber bundles are formed into a bullseye concentric configuration with the input fibers forming an outer ring (21) on the distal end and the output fibers in the center (22) of the distal end face.

The minimum distance between a fiber of the input bundle and a fiber of the output bundle can be varied to adjust tissue sampling depth which is also a function of the wavelength illuminating a sample. Generally, the sampling depth also increases with increases spacing between the illuminating and detector fibers. This spacing is, however, also adjusted to maintain useful signal level returned to the detector fibers. (Signal level also generally decreases with increasing spacing.)

This probe with spatially separated illuminating and detection fibers is useful in reflectance measurements, in order to assure that a discrete minimal optical path length through tissue is obtained and to avoid mere sampling of the most superficial elements of tissue. Previous work by Chance and Cui (Cui, W. et al. (1991), "Experimental study of migration depth for the photons measured at sample surface. Time resolved spectroscopy and imaging of tissues," S.P.I.E., 1431:180–190) suggests that the source to detector separation is roughly twice the average depth of penetration of light into tissue, and thus setting the spacing between the two sets of fibers between about 1 mm to about 3 mm is expected to have an average penetration of about 0.5 mm to about 1.5 mm, respectively. In addition, the use of a contacting probe reduced the surface specular reflection of light contributing to the detected signal to a minimum.

In operation, light from the source is delivered to a sample via the outer ring of fibers and light reflected from the sample is captured by the central fibers and conducted to the detector. For measurements in the visible wavelength region, the minimal fiber spacing used was about 1 mm, corresponding to an average sampling depth of approximately 0.4 mm (with a maximum depth of about 1.8 mm). For measurement in the near infra-red wavelength region, the minimum fiber spacing used was about 3 mm, corresponding to an average sampling depth of about 1.5 mm.

The system is optionally, but preferably, provided with a pulsed light source to allow for gated data collection. Selective data collection can be triggered or timed by a selected event, for example a physiological event. For example data collection from cardiac muscle can be triggered in in vivo measurements by the cardiac cycle, the respiratory cycle or both. The system is also optionally provided with a filter, e.g., a water filter (9), to decrease heating of the illuminated tissue sample. To avoid excessive and potentially damaging sample heating, it is preferable to employ a pulsed light source for timed data collection. For example, a mechanical, electrooptical or other type of light shutter 8 can be employed to provide for pulsed sample illumination.

The reflectance signal is conveyed to the detector, for example, through slit (11) and diffraction grating (12), to a photodiode array (13) to provide for photodiode detection as a function of wavelength. The signal from the detector, e.g., the photodiode array, can be read into an A/D converter (14) and the resulting digitized data conventionally stored on a computer system (23) which can also be employed for data analysis (e.g., PLS analysis).

The probe is formed from fiber optic bundles held in a desired configuration to achieve a desired minimum relative spacing between illuminating and detector fibers. For example, the fiber bundles can be inserted into an appropriately machined holder. The holder can be made of any inert, preferably non-toxic material, for example, metal, polymer material or plastic The distal end face of the probe is polished to obtain a highly smoothed surface, in which the fiber ends are substantially perpendicular to the plane of the distal end face. FIG. 2 illustrates a concentric bullseye arrangement of fiber. Alternate arrangements of illuminating and detector fibers at the distal end-face of the probe can be used. For example, a checkerboard arrangement of fibers which maintains the desired optimal spacing between illuminating an detector fibers can be employed. Another alternative useful configuration has spaced strips of illuminating and detector fibers.

For data collection, the distal end of the probe with input and output fibers is placed or held in contact with the tissue sample or at a selected position in contact with an organ, for example in contact with cardiac muscle or skeletal muscle. Contact with the sample can be continuous, intermittent or periodic to minimize motion effects. Sample measurement can be continuous, intermittent or periodic.

The method and device of the present invention can be employed for non-invasive measurement of muscle tissue. As used herein the term non-invasive includes measurements which inflict no damage to muscle tissue, yet which may require contact with muscle tissue. Methods of this invention also include those that are minimally invasive of tissue, for example those that may employ transillumination needle probes that must be inserted into the muscle tissue. A possible needle probe configuration combines two needle probes which are spaced apart, one of which carries the illuminating fiber and the other of which carries the detector fiber. A transmission spectrum of the tissue between the two needle ends can be obtained with such a probe. The method of this invention may employ contacting or non-contacting probes. A variety of methods for contacting the fiber optic probe with a tissue sample (either in vivo or in vitro) can be employed. For example, cardiac muscle measurements can be obtained by direct contact with the heart muscle during surgery or indirectly by minimally invasive techniques, for example, via catheter insertion of the probe or via insertion of the probe by transesophageal methods as used in transesophageal echo cardiography. Alternatively, a transillumination method can employ two inserted probes (one illuminating and one detecting) to collect transmission spectra of tissue between the probes. Transmission spectra of skeletal muscle may in some cases be obtained through the skin.

Multivariate analysis is employed to extract myoglobin saturation values from measured in vivo reflectance spectra of tissue. As an extension of linear regression, partial least squares analysis, which is preferred for this method, is used to evaluate multispectral data sets where several unknown concentrations of analytes are present. Partial least squares is a biased method of analysis (Sharaf, M. A. et al. (1986), Chemometrics, New York, Wiley) dependent upon the development of a model (i.e., the calibration set) which will preferentially fit certain elements of the data set. Partial least squares is based on an inverse model which attempts to solve the matrix equation $C=RB^t$ where C is a vector of concentration (or saturation) values which are correlated with R, the matrix of spectral responses, and by $B^t$, the transpose of the matrix of proportionality between R and C.

The purpose of the partial least squares regression is to determine B, the set of weighting factors for each wavelength which determine calibration coefficients to predict C, which in this case is the vector of saturation values. This can be achieved by determining an orthonormal decomposition of R which functionally redefines the spectral responses in a new coordinate system (Haaland, D. M. and Thomas, E. V. (1988), "Partial least squares methods for spectral analysis: Relation to other quantitative calibration methods and the extraction of qualitative information," Anal. Chem. 60:1193–1202; Arakaki, L. S. L. and Burns, D. H. (1992), "Multispectral analysis for quantitative measurements of myoglobin oxygen fractional saturation in the presence of hemoglobin interference," Appl. Spectrosc. 46:1919–1927).

Thus, one aspect of this invention is the development of a calibration set useful for multivariate analysis, particularly for partial least squares (PLS) analysis, that is robust for the quantitation of myoglobin fractional oxygen saturation from optical measurements (e.g., reflectance spectroscopy or transmission spectroscopy) of blood-perfused tissue in vivo. A calibration set is preferably developed for each type of tissue that is to be sampled, for different patient types (to compensate, for example, for possible difference due to age, health or presence of a given disorder).

The calibration set contains a plurality of spectra with optical properties similar to those (e.g., absorbers and or scatterers) which would be found in measured spectra (e.g., reflectance spectra or transmission spectra) obtained from blood-perfused tissue samples). The calibration set includes spectra of solutions which contain absorbances in the wavelength region of interest, e.g., the visible wavelength region (typically from about 400 to about 700 nm and preferably from about 515 to about 660 nm) and/or the near infrared wavelength region (typically from about 650 to about 1010 nm) from the four main chromophores in muscle: myoglobin and hemoglobin in their oxy- and deoxy-forms. The calibration set contains spectra having a constant total myoglobin concentration selected to approximately match the myoglobin concentration of the muscle tissue to be examined. The calibration set must also contain spectra having some variation in total hemoglobin concentration, hemoglobin oxygen saturation and myoglobin oxygen saturation. While muscle tissue contains other absorbing species, including the cytochromes, these species are typically present in significantly lower concentrations than myoglobin and hemoglobin, such that their effect on tissue spectra is less than about 10% and can be ignored without significant detriment to the accuracy of quantitation (Drabkin, D. (1950) J. Biol. Chem. 182:317–333). However, a calibration set for in vivo measurements in muscle tissue can be improved by inclusion of spectra containing the absorbances of other absorbing species present in muscle tissue, for example, appropriate cytochrome species found in muscle tissue. A calibration set which included cytochrome species would also contain spectra representing variation in cytochrome oxidation state. The range of variation in hemoglobin concentration, hemoglobin oxygen saturation, and myoglobin saturation and any other absorbing species represented in the calibration set is preferably selected to span the range of values expected to be encountered in tissue samples.

Each calibration sample from which a calibration set spectrum was obtained also contained a scattering agent which was selected to mimic the scattering observed in tissue at the wavelengths of interest. The range of levels of scattering represented in the calibration set is preferably selected to span the range of scattering observable in tissue samples.

In the calibration samples used to create the calibration set, the concentrations of absorbers and scattering agents are allowed to vary independently of one another. In tissue, the oxygen saturations and concentrations of hemoglobin and myoglobin may be quite different at any given time, since hemoglobin is present in the red blood cells circulating in the vasculature and myoglobin is found within myocytes. The calibration set must contain spectra with independent myoglobin and hemoglobin saturations, in order to quantitate myoglobin saturation.

In a single solution containing both myoglobin and hemoglobin, it is not possible to generate independent oxygen saturation of these species. Calibration set members containing absorbances resulting from independently controlled hemoglobin and myoglobin saturation levels were generated by mathematical addition of spectra obtained from individual solutions containing only myoglobin or only hemoglobin at a selected saturation level. Since, the sample depth of the reflectance fiber optic probe was not large enough to permit the collection of spectra through two cuvettes, reflectance myoglobin and hemoglobin spectra that were acquired separately were mathematically generated and included in the calibration set. Calibration set spectra also contained varying amounts of a scatterer.

If the total myoglobin concentration ([MbO$_2$]+[Mb]), total hemoglobin concentration ([HbO$_2$]+[Hb]), and the scattering coefficients of each measured tissue spectrum were known, a calibration set could be constructed for every combination. This approach is not practical for in vivo measurements, since individual animals and muscles have different hematocrits, tissue blood volumes, and myoglobin contents. These differences may cause relative changes in OD (optical density) values that do not necessarily correlate to myoglobin saturation. A simpler alternative used in the development of calibration sets of this invention is to use a single calibration set that brackets the values of total hemoglobin concentration, and scattering coefficients. A single value for total myoglobin concentration is used in all calibration set spectra. The PLS model resulting from the calibration set will as a result be sensitive to myoglobin saturation, but may be less affected by changes in scattering coefficients and hemoglobin concentrations than a model based on a calibration set containing spectra that have a single set of parameters.

The calibration sets exemplified herein that were developed for in vivo measurements in rat skeletal muscle or dog cardiac muscle, were developed employing rabbit hemoglobin or porcine hemoglobin, respectively and horse heart myoglobin. In general, it is not necessary in the method of this invention to employ hemoglobin and myoglobin of the mammal from which in vivo tissue spectra will be measured in the creation of the calibration set. It is not necessary to use human hemoglobin and human myoglobin to establish a calibration set for use in clinical measurements of this invention in human muscle tissue. However, some improvement in accuracy of myoglobin saturation determination by this method may be obtained, if hemoglobin and myoglobin of the appropriate mammal are used. It is not presently practical due to high cost and limited availability to use human myoglobin to establish a calibration set for human muscle tissue measurements.

It will be appreciated by those of ordinary skill in the art that genetic variants of hemoglobin and/or myoglobin may exist in a given individual and further that in certain circumstances variant adduct forms of hemoglobin or myoglobin may be present in a given individual at a given time. The terms hemoglobin and myoglobin are used herein in a general way, unless otherwise noted, to include proteins from different mammals, to include various genetic variants of the proteins and to include various adducts of these proteins.

A second aspect of the analysis of this invention involves the use of some form of mathematical manipulation to compensate errors due to scattering. In particular, derivatives of the spectra are used and more preferably second derivatives of the spectra are used. Scattering coefficients ($\mu_s$) in skeletal muscle vary greatly, judging from the wide range of values reported in the literature. At 633 nm, values for $\mu_s$ in muscle range from 0.41 to 22.9 mm$^{-1}$ (Cheong, W. F. et al. (1990) IEEE J. Quant. Elec 26:2166). Changes in scattering coefficients can have profound effects on peak shapes and optical densities (OD). Consequently, a PLS calibration (or related multivariate analysis) made on a calibration set with a particular set of scattering coefficients may not yield accurate determinations of myoglobin saturation from a prediction set (or collected data set) with different scattering coefficients. Spectral variations caused by differences in $\mu_s$ can be mistaken for differences in myoglobin saturation.

A brute-force and highly impractical way to handle this situation is to construct a PLS calibration set for every prediction set spectrum or measured spectrum that has a set of unique scattering coefficients. However, the scattering coefficients of the sample would still need to be measured independently.

Another approach is to remove the effects of scattering from prediction set spectra and to use a single calibration set composed of spectra without scattering. Hoffman et al used the Kubelka-Munk two-flux theory as a model for light scattering in tissue to do this (Hoffmann, J. et al. (1984) Adv. Exp. Med. Biol. 180:555; Hoffmann, J. et al. (1985) Adv. Exp. Med. Biol. 191:883). A transfer function was developed between absorbance spectra and diffuse reflectance spectra that were acquired from samples with the same absorbances in a scattering medium. Reflectance spectra were mathematically transformed into absorbance spectra with the transfer function. Myoglobin saturation was quantified with a least-squares analysis on the modified spectra, using absorbance spectra of myoglobin as a basis. In order to obtain accurate myoglobin saturations with this method, the transfer function must describe light scattering in tissue precisely. Models that are commonly used for scattering such as the Kubelka-Munk theory (Hoffmann, J. et al. (1984) Adv. Exp. Med. Biol. 180:555; Hoffmann, J. et al. (1985) Adv. Exp. Med. Biol. 191:883), the diffusion approximation (Marble, D. R. et al. (1994) Appl. Optics 33:1279), and Monte Carlo simulations (Flock, S. T. et al. (1989) IEEE Trans. Biomed. Eng. 36:1162) are approximations that assume simple tissue geometries and homogenous optical parameters. Detailed measurements of absorption and scattering coefficients in vivo are necessary to assess the applicability of such approximations to the transformation of reflectance into absorbance spectra.

The preferred approach of this invention for quantifying myoglobin saturation from reflectance spectra that may have different scattering coefficients is to use a single PLS calibration set containing spectra acquired in vitro from samples having an appropriately selected range of scattering. The effects of scattering on the spectra are decreased by using second-derivative spectra with respect to wavelength ($\lambda$). If the effects of scattering on spectra can be minimized sufficiently in both calibration and collected data sets, it is not necessary to match the scattering coefficients in the two data sets exactly to obtain accurate determinations using the PLS analysis. Neither tedious measurements of scattering coefficients nor a precise model for light scattering in tissue are required.

The following reasoning indicates that second-derivative spectra with respect to wavelength would be less sensitive to changes in scattering coefficients than the original OD spectra because of theoretical relationships between absorption coefficients, scattering coefficients, and spectral OD. A steady-state solution to the diffusion approximation for an infinite slab geometry is given by Cope et al. (1991) Proc. SPIE 1431:251.

$$\log (I_0/I) = A = [\sigma\rho - \ln(1+\sigma\rho)][\log e], \quad (3)$$

where A=attenuation (OD), $\rho$=distance between source and detected light, $\sigma = (3\mu_a(\mu_a+\mu'_s))^{1/2}$, $\mu_a$=absorption coefficient (OD/cm), and $\mu'_s$=reduced scattering coefficient (mm$^{-1}$). Reduced scattering coefficients are given by:

$$\mu'_s = \mu_s (1-g) \quad (4)$$

where g is the average cosine of the scattering angle at each scattering event.

Figure 1A:
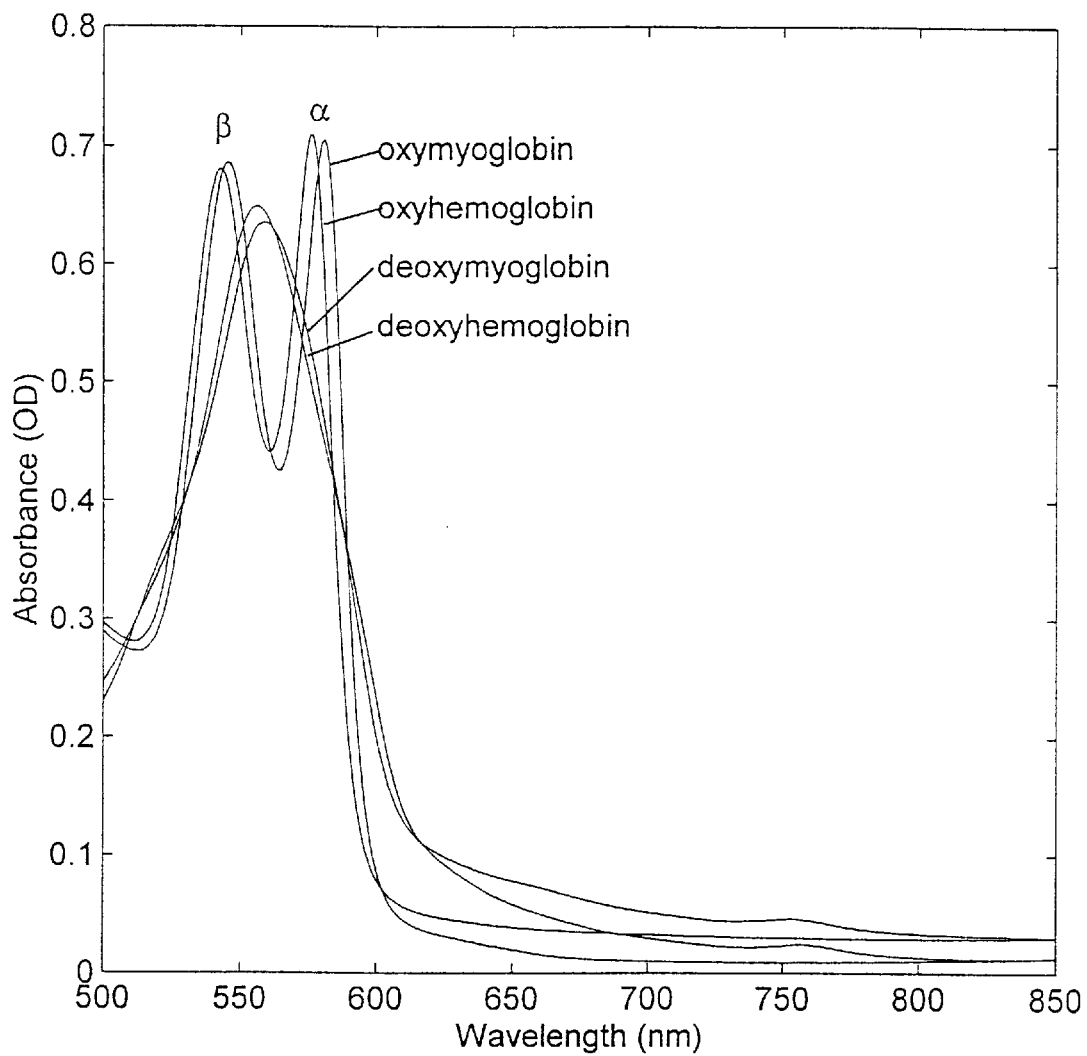
FIG. 1A is a plot of the visible and near-infrared absorption spectra of hemoglobin and myoglobin in the oxygenated and deoxygenated states. The difference in magnitude of absorption between the visible and near-infrared spectral regions can be seen for the four chromophores labelled in the plot. The plot shows the subtle, but, as illustrated herein, measurable difference in the $\alpha$ and $\beta$ peaks between oxyhemoglobin and oxymyoglobin. The differences between the spectra of the deoxy analogs is less apparent due to their width.
Figure 1B:
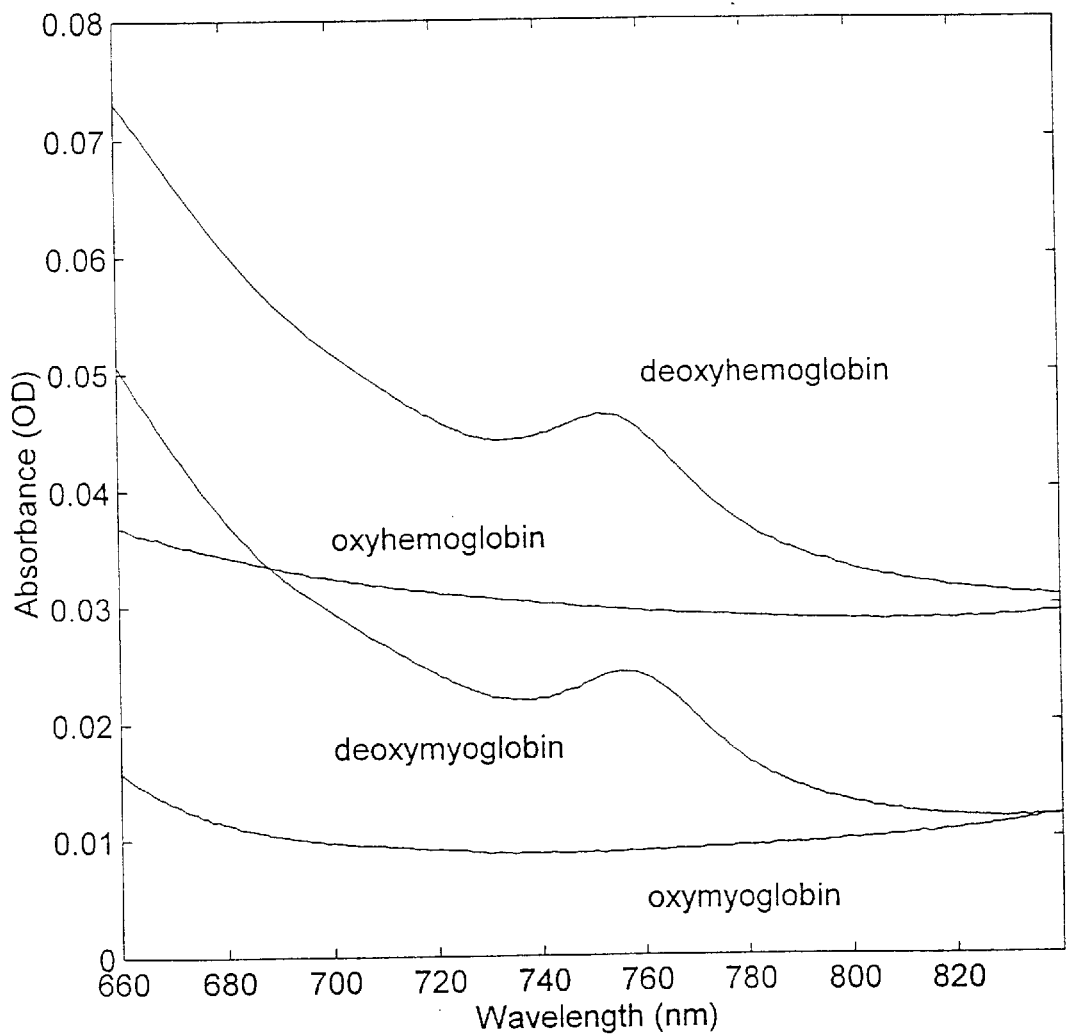
FIG. 1B is an expanded spectral plot of the near-infrared region of the spectra of FIG. 1A. Although the deoxy peaks are broad, the right shift of myoglobin relative to hemoglobin can be seen.
Figure 3A:
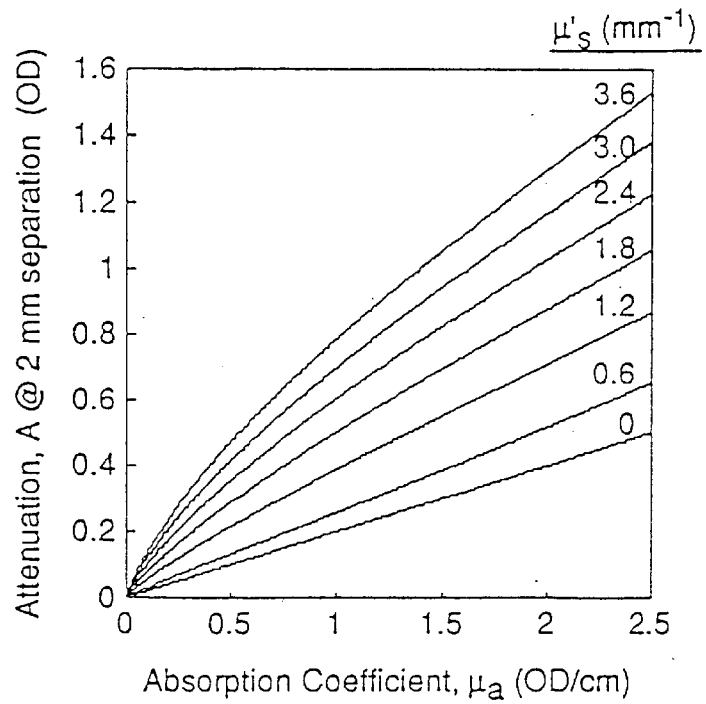
FIG. 3A shows the relationship between absorption coefficient and attenuation according to Equation 2. The separation between the light source and the detector is 2 mm.

FIG. 3A shows a family of A vs. $\mu_a$ curves according to Eq. 4, with each curve having a value of $\mu'_s$ between 0 and 3.6 mm$^{-1}$. At $\mu'_s$=0 mm$^-$, the relationship between $\mu_a$ and A is a line, a statement of the Beer-Lambert law. If the values for $\mu_a$ and $\mu'_s$ at a particular wavelength are known, the attenuation value, or the OD value of the spectrum at that wavelength, can be predicted by this model.

Figure 3B:
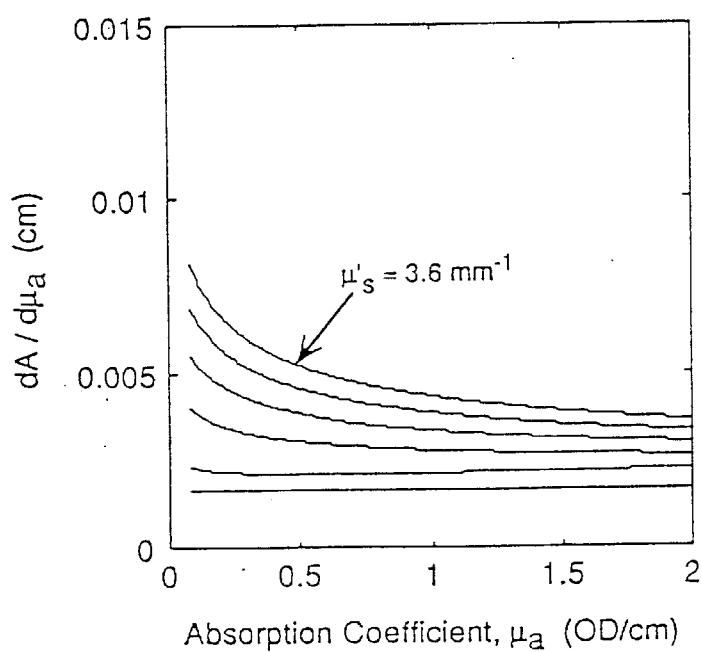
FIG. 3B shows the first derivatives of the curves shown in FIG. 3A. At high values of absorption coefficients, the first derivatives converge to the same values.

The first derivatives of curves in FIG. 3A are shown in FIG. 3B. At larger values of $\mu_a$ (above 1 OD/cm), the slopes of the A vs. $\mu_a$ curves are not strongly dependent on $\mu'_s$. When $\mu_a$ values are high, the relationship between $\mu_a$ and A is approximately linear with a slope that is nearly independent of $\mu'_s$.

$$\text{For } \mu_a > 1 \text{ OD/cm: } A(\mu_a, \mu'_s, \lambda) \approx m^* \mu_a(\lambda) + b(\mu'_s), \quad (5)$$

where m and b($\mu'_s$) represent the slope and y-intercepts of the lines, respectively. It should be noted that the threshold of $\mu_a$>1 OD/cm in Eq. 5 is dependent on ρ, the separation between the source and detected light. Nonlinearities in attenuation will shift this value at different separations. Second-derivative spectra with respect to wavelength will have only a weak dependence on $\mu'_s$:

$$\frac{d^2 A}{d\lambda^2} \approx m * \frac{d^2 \mu_a(\lambda)}{d\lambda^2} \quad (6)$$

Figure 4A:
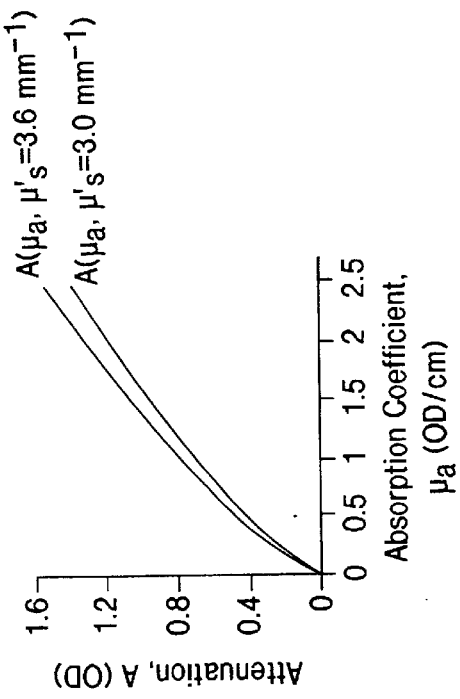
FIGS. 4A–D illustrate the relationship between absorption spectra and their second derivatives with respect to scattering coefficients. The curves in FIG. 4A are two attenuation spectra that have identical absorption coefficients (as shown in FIG. 4D). The OD curves are different because there is a 20% difference in $\mu'_s$ between them. The relationship between absorption coefficient and attenuation according to the diffusion approximation at these $\mu'_s$ values is shown in FIG. 4B. In these curves, similar slopes at high absorption coefficients lead to similar second-derivative spectra, as seen in FIG. 4C.
Figure 4B:
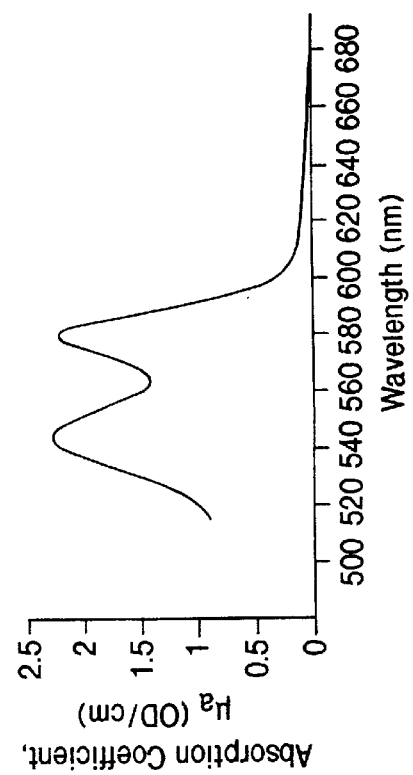
Figure 4C:
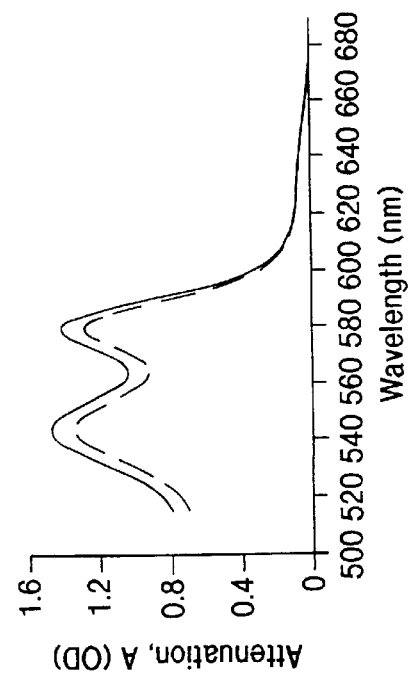
Figure 4D:
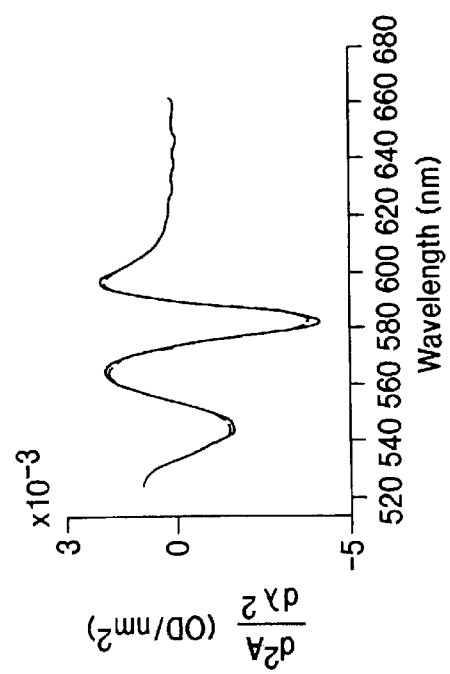

FIGS. 4A–D clarify this point. In FIG. 4A are shown two of the curves in FIG. 3A, those corresponding to $\mu'_s$=3.0 and 3.6 mm$^{-1}$. In a similar way to the transfer functions of Hoffmann et al., (Hoffmann, J. et al. (1984) Adv. Exp. Med. Biol. 180:555; Hoffmann, J. et al. (1985) Adv. Exp. Med. Biol. 191:883) these curves are transformations between absorption coefficients and measured attenuations (OD) in scattering media, according to the diffusion approximation. FIG. 4D shows a spectrum of absorption coefficients for oxymyoglobin (MbO$_2$). If a scattering sample had a value of $\mu'_s$=3.0 mm$^{-1}$, the absorption coefficient spectrum would be transformed through the lower curve of FIG. 4B, and the dashed attenuation spectrum in FIG. 4A would be observed. Similarly, if the sample had a reduced scattering coefficient of $\mu'_s$=3.6 mm$^{-1}$, the upper transformation curve of FIG. 4B would be used, resulting in the solid spectrum in FIG. 4A.

The difference between the measured OD values caused by a variation in $\mu'_s$ can be problematic for PLS predictions. A PLS prediction of myoglobin fractional saturation is the result of the dot product between the PLS calibration vector and a myoglobin spectrum (Haaland, D. M. and Thomas, E. V. (1988) Anal. Chem. 60:1193–1202). The two myoglobin OD spectra in FIG. 4A will produce different PLS estimates of myoglobin fractional saturation despite identical absorption coefficients that reflect a single value for myoglobin saturation. This potential error is entirely due to different scattering coefficients.

Since the slopes of the A vs $\mu_a$ curves in FIG. 4B are similar at high values of $\mu_a$, attenuation spectra (FIG. 4A) will have similar slopes in the same wavelength regions. Therefore, first derivatives of the attenuation spectra with respect to λ are expected to overlap significantly. The same arguments apply to second-derivative spectra, which are used because peaks in the second derivative occur at the same wavelengths as in the original spectra. Second derivatives of the attenuation spectra are shown in FIG. 4C. Using the second derivative increases the overlap between spectra with different $\mu'_s$ values, thereby removing most of the effects of variable scatter intensity.

The assumption in this model is that $\mu'_s$ values do not vary significantly with wavelength within each section of the spectrum where the derivative is calculated. The reduced scattering coefficient is wavelength-dependent, but it varies by only −0.0035 mm$^{-1}$/nm (data not shown) in dairy half-and-half that was used as a scatterer. This slope is similar to that of $\mu'_s(\lambda)$ measured in rat brain tissue (approximately −0.0027 mm$^{-1}$/nm) (Cope, M. et al. (1991) SPIE 1431:251). In the present method, second derivatives are calculated over sections of the spectrum that are 1.85 nm wide. The difference between $\mu'_s$ values at the extremes of this window is 0.006 mm$^{-1}$. This difference is small and will not invalidate the approximation made in Eq. 6.

Figure 5B:
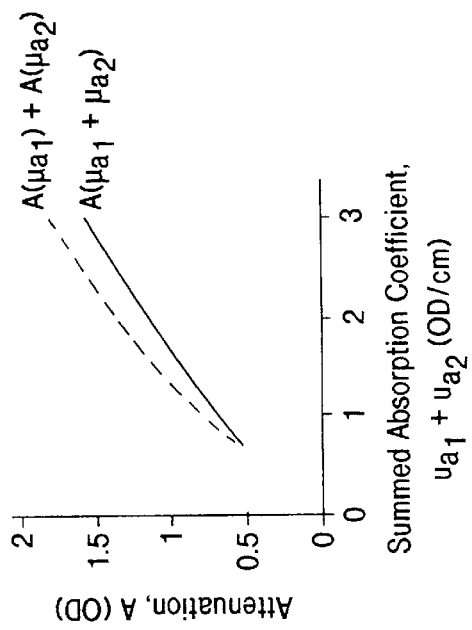
FIGS. 5A–D illustrate the relationship between absorption spectra and their second derivatives and the use of the second derivative for correction of errors due to the use of summed spectra in the calibration set. Individual absorption coefficient spectra for $MbO_2$ and $HbO_2$, along with their sum, are shown in FIG. 5D. At $\mu'_s$=3.0 mm$^{-1}$, the attenuation spectrum is the solid curve in FIG. 5A. This type of spectrum is expected in vivo, since both chromophores are present in a scattering medium. Individual attenuation spectra for $MbO_2$ and $HbO_2$ with $\mu'_s$=3.0 mm$^{-1}$ are also shown in FIG. 5A. The dotted curve is the sum of these attenuation spectra and is representative of in vitro calibration set spectra. Summed and mixed spectra (see text for description) have different transformations between summed absorption coefficients and attenuation, as seen in FIG. 5B. Similar slopes at high absorption coefficients lead to similar second-derivative spectra, as shown in FIG. 5C.
Figure 5D:
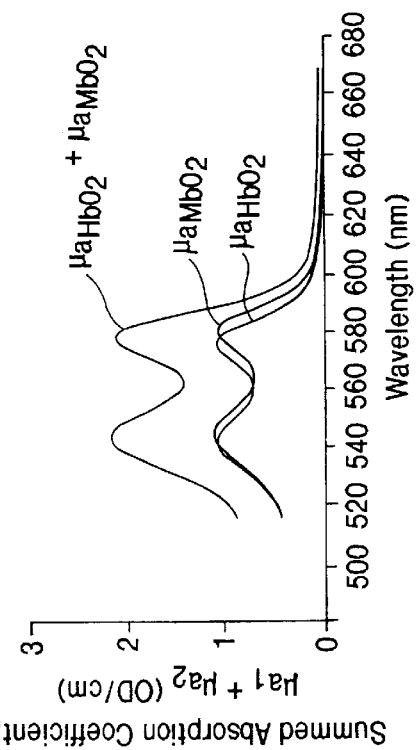
Figure 5A:
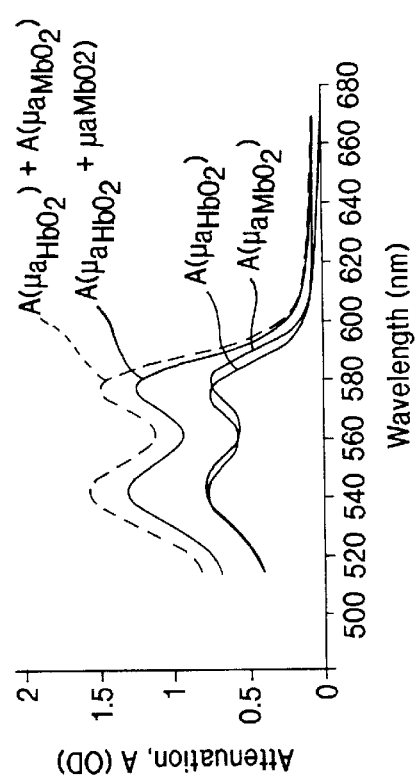
Figure 5C:
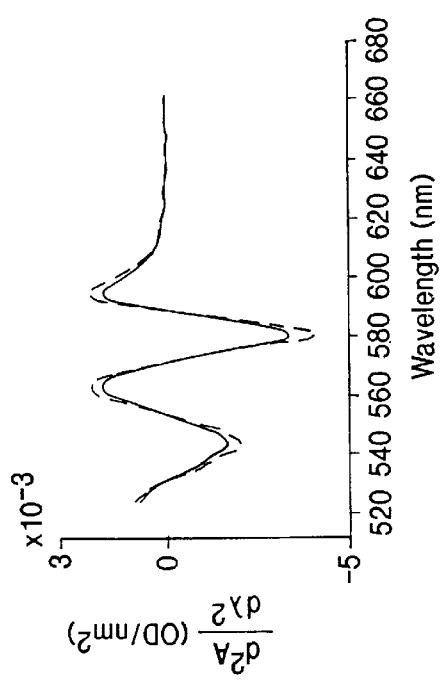

Spectra that are sums of myoglobin and hemoglobin spectra have different OD values from spectra of samples containing identical absorbers and scatterers in the same quantities, see FIGS. 5A–D. FIG. 5D shows absorption coefficient spectra of MbO$_2$ and oxyhemoglobin (HbO$_2$). If MbO$_2$ and HbO$_2$ were both present in a sample, the total absorption coefficient at each wavelength would be the sum of the individual absorption coefficients, also shown FIG. 5D. When taken through the scattering transformation at a $\mu'_s$ value of 3.0 mm$^{-1}$ (lower curve in FIG. 5B), the combined absorbances result in the OD spectrum drawn with a solid line in FIG. 5A. This is the spectrum that is expected in vivo. As the absorption coefficients of myoglobin and hemoglobin are mixed in the same sample, this type of OD spectrum will be referred to as a mixed spectrum.

In contrast, calibration set spectra are sums of myoglobin and hemoglobin OD spectra that include scattering. Individual MbO$_2$ and HbO$_2$ attenuation spectra are shown in the lower part of FIG. 5A. These spectra each have a $\mu'_s$ value of 3.0 mm$^{-1}$, the same value as in the mixed spectrum. The summed OD spectrum is shown with a dotted line, and has higher OD values than the mixed spectrum with the same original absorption coefficients.

Shown in FIG. 5B are the transformations between summed absorption coefficients and attenuation in a scattering medium for mixed (—) and summed OD (---) spectra. The mixed curve was obtained by adding incremental values of $\mu_a$ to a baseline value of $\mu_a$=0.8 OD/cm and $\mu'_s$=3.0 mm$^{-1}$. It is a portion of the $\mu'_s$=3.0 mm$^{-1}$ curve in FIG. 3A. The summed curve (---) was obtained by adding the OD values associated with incremental increases in $\mu_a$ to the OD value of the baseline point. All addends had a $\mu'_s$=3.0 mm$^{-1}$. The difference between the two transformation curves expresses the expected difference in OD between mixed spectra acquired in vivo and summed OD spectra in the calibration set when absorption and scattering coefficients are the same.

As seen in FIG. 5B, the slopes of the mixed and summed transformations approach the same value at high absorption coefficients. Using the argument presented by Eqs. 5 and 6, second derivative spectra of summed OD spectra will be approximately equal to second derivatives of mixed spectra with the same absorption and scattering parameters. This is demonstrated in FIG. 5C. The solid and dashed derivative spectra correspond to the mixed and summed OD spectra shown above, respectively. The increased overlap indicates that a calibration set composed of second-derivative summed spectra is appropriate for prediction set spectra acquired in vivo.

In order for second derivatives of summed and mixed spectra with the same optical parameters to be similar, both addends must have relatively high absorption coefficients. They must correspond to portions of the curves in FIGS. 3A–B where $dAd\mu_a$ is rather independent of $\mu'_s$. The worst-case situation occurs when the sum of absorption coefficients is close to 0.

In specific embodiments of this invention, myoglobin oxygen saturation in a given measured spectrum is calculated by multiplying that spectrum by a vector that encompasses the PLS model (the calibration coefficients). Specifically, myoglobin oxygen saturation is the linear summation of the products of the measured spectra at a given wavelength and the calibration coefficient at that wavelength. These calculations will be direct determinations of myoglobin fractional oxygen saturation when the total myoglobin concentration of the collected data set is equal to that of the calibration set. However, if the myoglobin concentrations in the data and calibration sets differ, the calculations made using the calibration coefficients will be linearly related to myoglobin fractional saturation. The values obtained can be scaled or normalized to provide absolute or normalized values of myoglobin saturation. A variety of methods for scaling the determined values are available and can be readily applied to this method.

PLS results can be scaled to obtain absolute myoglobin saturation values if four assumptions are made: i) values calculated by PLS are linear with myoglobin fractional saturation; ii) myoglobin concentration is constant in both the calibration and any prediction sets or any measured data; iii) two different myoglobin saturations are known within each prediction set; and iv) changes in myoglobin concentration, hemoglobin concentration, or scattering coefficients do not affect the linearity between PLS estimates and myoglobin saturation. The first assumption is valid, as evidenced by in vitro experiments that were done in solutions with negligible scattering (Arakaki, L. S. L. and Burns, D. H. (1992) Appl. Spectrosc. 46:1919; Schenkman, K. A. and Burns, D. H. (1994) Proc. SPIE 2131:468) and by in vitro trials in this paper (see Results and Discussion). The second assumption is necessary to ensure uniform scaling over all PLS estimates made from a given prediction set. Myoglobin concentrations in prediction sets acquired in vivo are assumed to remain constant over a short-term experiment because myoglobin is not washed out of the tissue and is not rapidly synthesized or metabolized. The third item allows a line to be defined between the two known points, where myoglobin fractional saturations are plotted on the abscissa and PLS estimates are plotted on the ordinate. The slope and intercept of this line determine the relationship between PLS estimates and myoglobin saturation for a prediction set. All other points in the prediction set can then be scaled by this line. The fourth assumption has also been demonstrated to be valid. In addition, it was found that changes in optical parameters that affect spectral OD values do not affect the linearity between PLS estimates and myoglobin saturation.

EXAMPLES

Example 1

Reflectance Measurements in the Visible Wavelength Region

An optical spectrophotometer, similar to that of the schematic of FIG. 2, was assembled to acquire spectra between 515 and 660 nm. The light source was a 150-watt halogen bulb. A custom-made bifurcated fiber optic probe containing two fiber optic bundles was used to separately transmit light to and carry reflected light from the sample. The distal end of the probe is formed as illustrated in FIG. 2 by concentrically arranging separate fiber optic bundles: the central bundle is 1.8 mm in diameter and carries light from the sample to the spectrograph and a 1.1 mm-diameter ring of fibers around the central bundle delivers light to the sample. The source and detection fiber bundles are thus separated by a minimum distance of 1 mm. This separation results in a maximum sampling depth for visible light of about 1.8 mm (Arakaki, L. S. L. (1995) *An Optical Method for Myoglobin Oxygenation Measurements in the Blood-Perfused Rat Hind Limb*, Doctoral Dissertation, University of Washington).

Light reflected from the sample and captured by the central fiber bundle was focused onto a 500-$\mu$m slit, which was attached to a spectrograph (American Holographic, Littleton, Mass.). The diffraction grating used had an average dispersion of 25 nm/mm. A 512-element photodiode array with a pixel size of 2.5 mm×25 $\mu$m (H×W) was used as a detector. A Macintosh II computer (Apple Computer, Inc., Cupertine, Calif.) equipped with a 100-kHz, 12-bit A/D board (National Instruments, Corp., Austin, Tex.) was used to control the diode array clock cycles and to store the digitized data. Typical spectra were composed of 100 averaged acquisitions collected in 12 sec.

Horse heart myoglobin was obtained in lyophilized form (Sigma Chemical Co., St. Louis, Mo.). Combining 300 mg of myoglobin with 3 mL of 50 mM phosphate buffer at pH 7.6 resulted in a concentrated metmyoglobin solution. The reduction of metmyoglobin was based on a method described by Bauer and Pacyna (Bauer, C. and Pacyna, B. (1975) Anal. Biochem. 65:445). A 22×1 cm (L×diam.) column was filled with G-25-300 Sephadex (Sigma Chemical Co., St. Louis, Mo.) that was equilibrated with the phosphate buffer at 4° C. Then a 4 mL volume of 108 mM sodium dithionite was placed on the column, followed by the metmyoglobin solution. Sodium dithionite was effective in immediately reducing the heme iron. The relatively large myoglobin molecules (MW 18,800) were eluted before excess sodium dithionite and reaction by-products arrived at the bottom of the column. Myoglobin solutions were stable for at least 24 hours when stored at 4° C. Concentrations of oxymyoglobin solutions were calculated based on an absorptivity of 1.44 OD/(mM mm) at 580 nm (Antonini, E. and Brunori, M. (1971) *Hemoglobin and Myoglobin in Their Reactions with Ligands* (North-Holland Publishing Co., Amsterdam, ed., p. 19).

Hemoglobin solutions were obtained from heparinized rabbit blood. Addition of distilled water caused the red blood cells to lyse, resulting in a dilute hemoglobin solution. Oxyhemoglobin concentrations were calculated assuming an absorptivity of 1.46 OD/(mM m) at 577 nm (Antonini, E. and Brunori, M. (1971) *Hemoglobin and Myoglobin in Their Reactions with Ligands* (North-Holland Publishing Co., Amsterdam, ed., p. 19). Deoxyhemoglobin was obtained by the addition of a small amount of sodium dithionite to oxyhemoglobin.

Dairy half-and-half was used as a scatterer in solutions used to develop the calibration set. The mean particle diameter was 3 $\mu$m, as measured using an optical microscope with a calibrated scale. A transmission spectrum of a dilute solution of half-and-half was used to determine its scattering properties. It was assumed that light absorption by the half-and-half was small and that the decrease in intensity was entirely due to scattering. These OD values and the % concentration were used to calculate $\mu_s$ values as a function of wavelength. A g value of 0.85, measured in non-dairy creamer in this wavelength range (Marble, D. R. et al. (1994) Appl. Optics 33:1279), was used in Eq. 4 to calculate $\mu_s(\lambda)$.

Computer simulations were employed to better understand how using second-derivative spectra and summed spectra influenced PLS results. In addition, the simulations expedited the collection of the in vitro calibration set. Through different trials, the relationships between the composition of the calibration and prediction sets and the accuracy of PLS determinations could be studied.

Synthetic spectra were derived from a few spectra collected in vitro. Transmission spectra of oxymyoglobin, deoxymyoglobin, oxyhemoglobin, and deoxyhemoglobin solutions at the same concentrations and without scatterer were acquired. Simulated spectra with intermediate fractional saturations of myoglobin were derived by adding oxymyoglobin and deoxymyoglobin spectra in fractional combinations. Concentration differences were obtained by multiplying myoglobin or hemoglobin spectra by a constant factor. Eq. 3 was used to simulate attenuation spectra with myoglobin or hemoglobin and scattering. Myoglobin or hemoglobin absorbance spectra that were normalized by the cuvette pathlength were inserted as $\mu_a$ values. Reduced scattering coefficients measured from the scatterer were inserted as $\mu'_s$ values.

The myoglobin concentration of the calibration set spectra for this experiment was 50 $\mu$M. This value is in the range of myoglobin contents for rat hind limb skeletal muscle given in the literature (Anthony, A. et al. (1959) Am. J. Physiol. 196:512; Harms, S. J. and Hickson, R. C. (1983) J. Appl. Physiol.: Respirat. Environ. Exercise Physiol. 54:798). As discussed above, spectra with ranges of hemoglobin concentrations and scattering values were included in the calibration set. Spectra representing hemoglobin concentrations of 25 $\mu$M, 100 $\mu$M, and 200 $\mu$M were included. At each [hemoglobin]:[myoglobin] ratio, a set of spectra containing 40, 50, or 60% volume of scattering agent were included. The values for $\mu_s$ at 633 nm for these % volumes were 15.4, 19.2, and 23.1 mm$^{-1}$, respectively. These are in the range of $\mu_s$ measured by others in muscle tissue (Cheong, W. F. et al. (1990) IEEE J. Quant. Elec 26:2166). The corresponding $\mu'_s$ values are 2.31, 2.88, and 3.46 mm$^{-1}$. There were 144 spectra in the synthetic calibration set.

Mixed prediction set spectra were also simulated. The construction differed from that of the summed spectra in that myoglobin and hemoglobin absorption coefficients were added together before scattering was incorporated with Eq. 3. As with the summed spectra, noise was added to mixed spectra. Second derivatives were used in all simulated prediction sets.

Calibration set spectra were produced by summing the oxyhemoglobin attenuation spectrum with a series of myoglobin attenuation spectra with different fractional saturations. Sums of the deoxyhemoglobin and myoglobin spectra were also included in the calibration set. Noise that was normally distributed with a standard deviation of approximately 0.0015 OD was added to each spectrum. Spectra acquired from muscle tissue in vivo were found to have an average standard error of 0.0015 OD relative to smoothed versions of the same spectra. Second derivatives of each spectrum were used in the calibration set.

In all in vitro trials, the bacteria E. coli was used to vary the pO$_2$ of myoglobin solutions. E. coli solutions in the stationary phase were obtained by allowing 100 $\mu$L of the bacteria to incubate overnight at room temperature in 10 mL of nutritive broth. After introducing 400 $\mu$L of E. coli to a total of 1.75 mL of myoglobin, hemoglobin, and scatterer, the bacteria metabolized the dissolved oxygen in solution in 30 to 50 minutes.

Independent measurements of myoglobin fractional saturation were employed to evaluate the accuracy of PLS estimates. A Clark-type oxygen electrode (Instech Laboratories, Plymouth Meeting, Pa.) was used to measure the pO$_2$ in solution simultaneously with spectral acquisitions. These pO$_2$ values are related to myoglobin fractional saturation by myoglobin oxygen dissociation curves, which are temperature-dependent.

In construction of the in vitro calibration set, the fmal concentration of myoglobin was 50 $\mu$M in all calibration set spectra. Three data sets were collected, where the scatterer comprised 40, 50, or 60% of the total volume. The remainder of the total volume of 1.75 mL was filled with 400 $\mu$L of E. coli in suspension and 50 mM phosphate buffer at pH −7.6. Spectra were acquired over the entire range of myoglobin oxygenation, and fractional saturation values were determined by CLS analysis. Eight spectra from each of the three data sets were used in the calibration set. These spectra were chosen to span the range from 0 to 1 evenly. Oxyhemoglobin and deoxyhemoglobin solutions with fmal concentrations of 25 $\mu$M, 100 $\mu$M, and 200 $\mu$M were used. At each of these concentrations, scatterer was added in 40%, 50% and 60% volume fractions, and the remainder of the volume was filled with the phosphate buffer.

The calibration set consisted of summations of eight myoglobin spectra with oxyhemoglobin or deoxyhemoglobin spectra. In each case, volume fractions of scatterer in myoglobin and hemoglobin spectra were matched. Since there were sixteen summed spectra at each of three hemoglobin concentrations at three volume fractions of scatterer, there were a total of 144 spectra in the calibration set.

Several prediction sets from solutions containing myoglobin, hemoglobin, scatterer, and E. coli were collected. These spectra were intended to mimic the situation in vivo where both absorbers are present without summing of myoglobin and hemoglobin spectra. Although the fractional saturations of myoglobin and hemoglobin are not independent in mixed solutions, they were needed to assess the applicability of the summed calibration set to in vivo conditions.

Temperature and pO$_2$ readings were collected with each spectrum. All prediction set spectra were collected within either of the two temperature ranges of the measured myoglobin dissociation curves. The fractional saturation associated with any pO$_2$ value was calculated with Eq. 2. Errors in scaled PLS estimates were assessed by comparison with these fractional saturation values.

Discrete second differences were used to approximate second derivatives, and were calculated from each OD spectrum before PLS calibration or analysis. Spectra were first smoothed with a window of seven points, which corresponds to a span of 3.65 nm. Smoothing reduces the noise in the difference spectra (Holler, F. et al. (1989) Appl. Spectrosc. 43:877). The second difference value at a particular wavelength is equal to the sum of spectrum values ±1.85 nm from that wavelength minus two times the value at the central wavelength. Because the difference operation zeroes the first and last thirteen points, these points were omitted from each spectrum. There were a total of 213 points per spectrum after truncation.

Partial least squares was used to determine myoglobin fractional saturation from spectra that contained myoglobin absorbances. Details of the PLS algorithm are given in several sources (Haaland, D. M. and Thomas, E. V. (1988) Anal. Chem. 60:1193; Lorber, A. et al. (1987) Chemom. 1:19; Martens, H. et al. (1987) J. Chemom. 1:202; Beebe, K. R. and Kowalski, B. R. (1987) Anal. Chem. 59:1007). For each prediction set, the number of significant factors is determined from PRediction Error Sum of Squares (PRESS) values calculated for each factor. PRESS values are calculated as the sum of the squares of residuals between PLS estimates and known S values for all spectra in a prediction set. The ratios between PRESS values for each factor and the minimum PRESS value were calculated. An F-test at 75% significance on the ratios is an empirical criterion used to determine the minimum number of statistically significant factors (Haaland, D. M. and Thomas, E. V. (1988) Anal. Chem. 60:1193).

Accurate determinations of myoglobin saturation by PLS require that spectra in the calibration and prediction sets have similar spectral features (e.g., peak shape, position, and OD). The Mahalanobis distance is a metric for outlier detection that was used to compare the calibration and prediction sets. It has been used with near-infrared spectra to qualify prediction set spectra for a linear regression (Whitfield, R. G. et al. (1987) Appl. Spectrosc. 41:1204), and as a classifier for spectra from different samples (Mark, H. L. and Tunnell, D. (1985) Anal. Chem. 57:1449). Mahalanobis distance calculations were based on an algorithm outlined by Shah and Gemperline (Shah, N. K. and Gemperline, P. J. (1989) Trends Anal. Chem. 8:357). A principal component analysis is first done on the calibration set spectra. Scores for each of the first few statistically significant principal components are determined for each spectrum in a prediction set. A Mahalanobis distance is defined as the n-dimensional geometric distance between a spectrum's scores and the mean of scores from the calibration set spectra. Here, n represents the number of principal components used. Since the scores of a prediction set spectrum are calculated from principal components derived from the calibration set, the Mahalanobis distance quantitatively represents the difference in spectral character between this spectrum and the spectra in the calibration set. Each Mahalanobis distance is associated with a probability value according to the chi-squared distribution. Spectra with a probability value between 1.0 and 0.05 are classified as members of the calibration set, and those with probability values less than 0.05 are labeled as outliers (Shah, N. K. and Gemperline, P. J. (1989) Trends Anal. Chem. 8:357).

A calibration set containing spectra with ranges of scattering and absorption coefficients was employed. PLS analysis was used to calculated values of myoglobin fractional saturation from all prediction sets and the values obtained from this analysis were scaled. This process is valid if PLS estimates are linear with myoglobin fractional saturation despite changes in [myoglobin], [hemoglobin], and $\mu'_s$. These linearities were tested in a set of seven simulations shown in Table I. Values for [myoglobin], [hemoglobin], and $\mu'_s$ in the prediction sets were each increased and decreased by 50% relative to the median values of the calibration set ([myoglobin]=50 $\mu$M, [hemoglobin]=100 $\mu$M, and % volume scatterer =50%).

Figure 6:
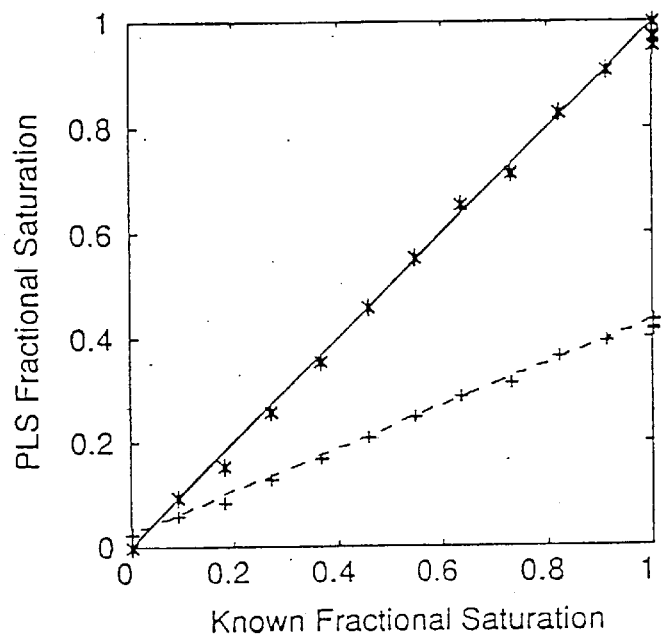
FIG. 6 shows a graph of PLS estimates for a simulated prediction set (see Example 1) with [myoglobin]=25 $\mu$M, half that of the median value in the calibration set (+). [Hemoglobin] and $\mu'_s$ are equal to the median values in the calibration set. Unscaled PLS values do not span the full range of myoglobin fractional saturation from 0 to 1. After scaling between two points where fractional saturation is known, accurate estimates of myoglobin saturation are obtained (*). The solid line is the line of unity.

Unscaled (+) and scaled (*) PLS estimates for the prediction set with decreased [myoglobin] (third row of Table I) were compared to known myoglobin fractional saturation (FIG. 6). The unscaled PLS estimates did not span the full range of myoglobin saturation from 0 to 1 since maximum OD values of spectra in the prediction set were smaller than those of the calibration set. However, a two-point scaling using the line between the points at known myoglobin fractional saturations of 0 and 1 resulted in accurate estimates of myoglobin saturation.

After scaling, standard errors (SE) relative to known values ranged from 0.008 to 0.053. High correlation coefficients ($R^2$) were obtained for all simulations, including those where the prediction set parameters were outside the bounds of the calibration set. These trials support the hypothesis that PLS estimates are linear with myoglobin fractional saturation. They also show that changes in [myoglobin], [hemoglobin], and $\mu'_s$ produce only linear changes in PLS estimates. Therefore, PLS estimates may be scaled between two known values of myoglobin fractional saturation if scattering coefficients, [myoglobin], and [hemoglobin] are constant in the prediction set.

Figure 7:
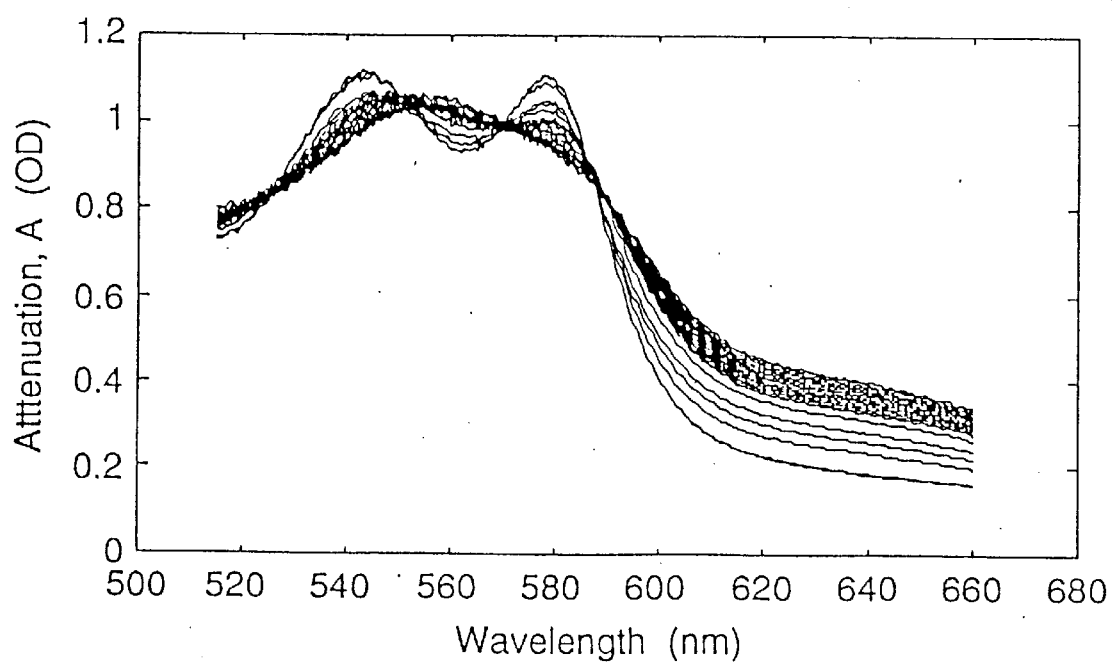
FIG. 7 illustrates reflection spectra acquired in vitro with [myoglobin]=50 $\mu$M, [hemoglobin]=150 $\mu$M, and 55% scatter by volume as described in Example 1.

Several physiological states in vivo were approximated in vitro. For example, a moderate increase in blood volume relative to the median values in the calibration set of 50 $\mu$M myoglobin, 100 $\mu$M hemoglobin, and 50% volume scatterer was assumed to be 50 $\mu$M myoglobin, 150 $\mu$M hemoglobin, and 55% scatterer. A spectral data set with these parameters is shown in FIG. 7. The $pO_2$ values associated with these spectra ranged from 0 to 155 Torr. After a two-point linear scaling of the PLS estimates, SE=0.089 and $R^2$=0.951.

Scaled PLS estimates are generally lower than the line of unity, especially at the lower values of S. The cause for this is a substantial drift in oxygen electrode readings at low $pO_2$ values. As the electrode readings continued to decrease, the spectral appearance of deoxymyoglobin changed very little. Similar PLS estimates were attributed to different "known" saturation values. In particular, the value at $pO_2$=0 is noticeably divergent from the line all previous points have formed. Performing a two-point scaling based on this erroneous $pO_2$=0 endpoint caused the intermediate fractional saturation estimates to be low after scaling.

An alternative scaling method used the best-fit line between the unscaled PLS estimates. The slope and intercept of this line were used to scale all of the points. The erroneous $pO_2$=0 point was not weighted as heavily, improving the SE to 0.064 and $R^2$ to 0.953 (Table II). Although the two-point scaling was not optimal for these trials in vitro, it should be appropriate for spectra collected in vivo, where the oxygen electrode is not used. The computer simulations presented in Table I demonstrate that the two-point scaling method works well when nonlinearities introduced by the electrode are not present.

Other [hemoglobin]:[myoglobin] ratios and % volume scatterer combinations were constructed in different prediction sets. All of the unscaled PLS estimates from these prediction sets were scaled using the best-fit line as described above. The results are shown in Table II. The maximum SE value was 0.082.

The first section of Table II contains examples of prediction set spectra where [myoglobin], [hemoglobin], and scattering levels were bounded by those of the calibration set. Other trials were performed where parameters of the prediction set spectra were outside those of the calibration set, and these are listed in the lower section of Table II. After scaling, the standard errors of the estimations from these prediction sets were similar to standard errors of estimations from data bounded by the calibration set. This implies that the in vitro calibration should be useful for spectra acquired in vivo, where [hemoglobin], [myoglobin], and scattering coefficients will be unknown and are likely to be different from calibration set values.

Mahalanobis distances were used to determine whether the in vitro calibration set was similar enough to the prediction sets for an appropriate PLS model to be made. Table II shows that none of the in vitro prediction set spectra were outliers of the calibration set. Probabilities derived from the Mahalanobis distances of the prediction set were well above the p=0.05 threshold that was chosen to demarcate outliers of the calibration set (Shah, N. K. and Gemperline, P. J. (1989) Trends Anal. Chem. 8:357). This analysis indicates that the calibration set is appropriate for all prediction sets over the range of myoglobin and hemoglobin concentrations and saturations and $\mu'_s$ values studied. Variations in spectral appearance between summed and mixed spectra were reduced in the second derivative.

A practical issue that arises when using a PLS model is the determination of the appropriate number of factors to use. The number of optimal factors listed in Tables I and II were obtained from PRESS values and an F-test for each prediction set. Generally, the number of optimal factors was three. For spectra acquired in vivo, three factors will be used because it is a simple model that is capable of yielding accurate estimates of myoglobin fractional saturation.

Spectra were acquired from the tibialis anterior of the rat hind limb with the same instrumentation and fiber optic probe. After a control period of 24 seconds, ischemia was imposed on the hind limb by temporary occlusion of the femoral artery. The ischemic period lasted for 2.2 minutes, after which blood flow was re-established and the muscle was allowed to recover.

Figure 8:
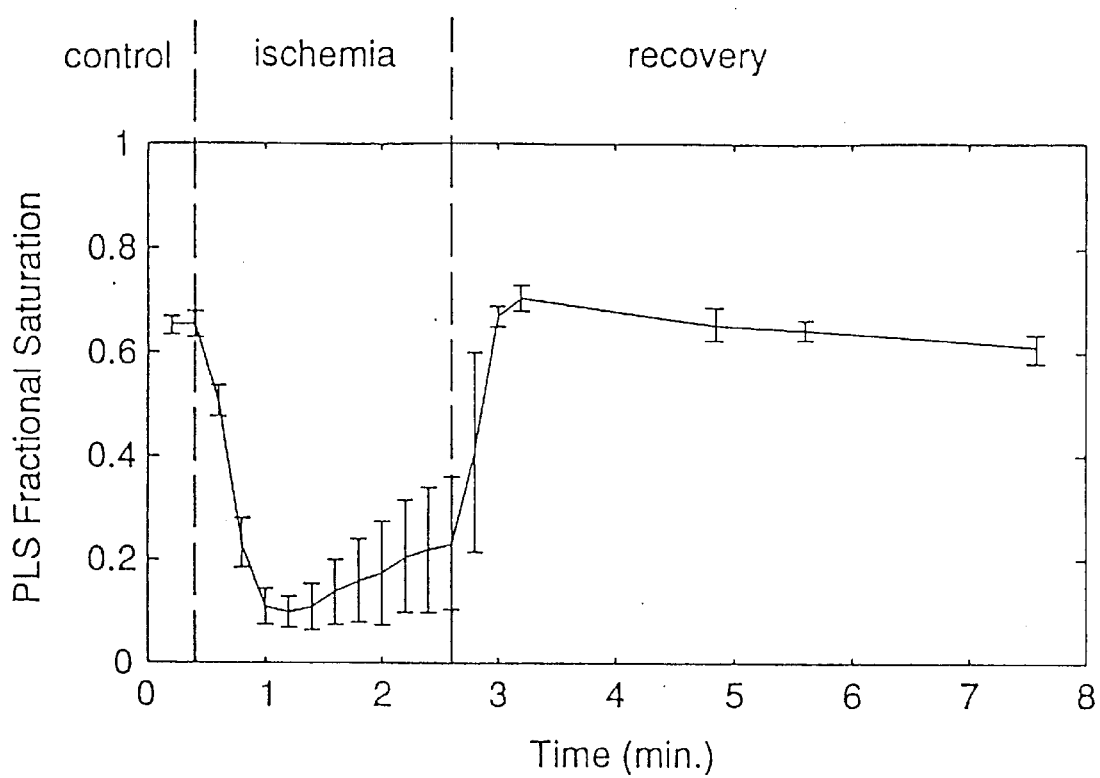
FIG. 8 is a graph of the mean ±SD for myoglobin fractional saturation determination in three consecutive ischemic trials in the rat hind limb (Example 1). Ischemia was imposed by temporary occlusion of the femoral artery. These results are consistent with logical expectations for an ischemic perturbation and are preliminary evidence that the summed, in vitro calibration set provides an appropriate model for in vivo measurements.

Mahalanobis distances from three consecutive ischemic trials in a rat ranged from 0.438 to 0.944. All p-values were well above the threshold of 0.05, indicating that the in vitro calibration set provides an appropriate model for these in vivo measurements. Myoglobin saturations in FIG. 8 are the mean ±SD of the three ischemic trials. PLS values were scaled between a myoglobin S value of 0.75 at rest (Gayeski, T. E. J. et al. (1985) Am. J. Physiol. 248:H914) and a value of 0, obtained after the rat's death. Rats were sacrificed with an anesthetic overdose. Myoglobin saturation repeatedly decreased during occlusion and then rebounded upon restoration of blood flow. These data indicate that determinations of myoglobin fractional saturation can be made from blood-perfused tissue in vivo.

Example 2

Reflectance Measurement in the Near-Infrared Wavelength Region

Spectral acquisition from cardiac tissue samples was performed using a fiber optic based spectrophotometer as illustrated in FIG. 2. Illumination was provided to the tissue from a custom-built current controlled 150 watt quartz-tungsten-halogen lamp via a bifurcated optical fiber bundle. The light source was equipped with a timed mechanical shutter and the light was transmitted through a one-inch water filter to decrease heating of the illuminated tissue. Reflected light from the sample was received via a detection optical fiber bundle and transmitted to the diffraction grating in the spectrograph (American Holographics model #100S). The diffracted light was then focused onto a 512 pixel diode array photodetector (Hamamatsu model S3901-512Q). The signal from the photodetector was read out onto a 16 bit 100 kHz A/D converter (National Instruments #AT-MIO-16X) and the resultant information stored on a 486-66 MHz personal computer.

Transmission spectra for the partial least squares calibration were acquired using ¼" fiber optic bundles to transmit and collect the light. Incident light was transmitted through two 1 cm path length glass cuvettes before being returned to the spectrometer.

Myoglobin solution was made from commercially-available horse heart myoglobin (#M1882 Sigma Chemicals, St. Louis, Mo.) dissolved in 50 mM phosphate buffer at pH 7.6. Commercially-available myoglobin comes as oxidized metmyoglobin. To reduce the metmyoglobin to the physiologically active state, excess sodium dithionite was added to the solution which was then separated on a 25 cm sephadex chromatography column under nitrogen at 4° C. The myoglobin solution was then equilibrated with room air to form oxymyoglobin. The solution was diluted with buffer to achieve a maximal O.D. of approximately 1.0 in the visible spectral region so that the entire spectrum fell into the range 0.15<O.D.<1.0 where Beer's Law is most accurate (van Assendelft, O. W. (1970), *Spectrophotometry of Haemoglobin derivatives*. Assen, the Netherlands, Royal VanGorcum LTD). Hemoglobin solution was prepared from porcine blood diluted with distilled water to lyse the blood cells. The dilute hemoglobin solution was decanted off the top to remove cellular debris, and placed into two 1 cm glass cuvettes. The solution was further diluted to achieve a maximal O.D. of approximately 1.0 in the visible spectral region, as above. Deoxyhemoglobin solution was made by the addition of sodium dithionite to one of the two cuvettes, which was then capped.

In vitro spectra from 500 to 1010 nm were collected from a light path traversing two 1.0 cm glass cuvettes, one containing myoglobin and the other hemoglobin. Use of two cuvettes allowed for independent variation of the oxygen saturation of the myoglobin and hemoglobin solutions. A slow deoxygenation of the myoglobin solution over time was achieved by the addition of 75 mg of dextrose and 0.4 ml of an *E. coli* solution. The myoglobin cuvette was then capped. Spectra were obtained from the myoglobin solution alone with a blank solution in the second cuvette, and from the myoglobin solution in combination with either the oxyhemoglobin or deoxyhemoglobin alternately placed in the second cuvette, at 21° C. This allowed for independent oxygenation of the myoglobin solution with no hemoglobin, and oxyhemoglobin or deoxyhemoglobin as the interferent. Spectra were recorded approximately every 20 seconds, thus resulting in acquisition of spectra from the myoglobin solution alone (blank solution in the second cuvette) about once per minute. Actual time of each spectral acquisition was recorded. These spectra were used to validate the PLS method using non-scattering solutions. Subsequently spectra from scattering solutions were used to generate a calibration set.

Figure 9:
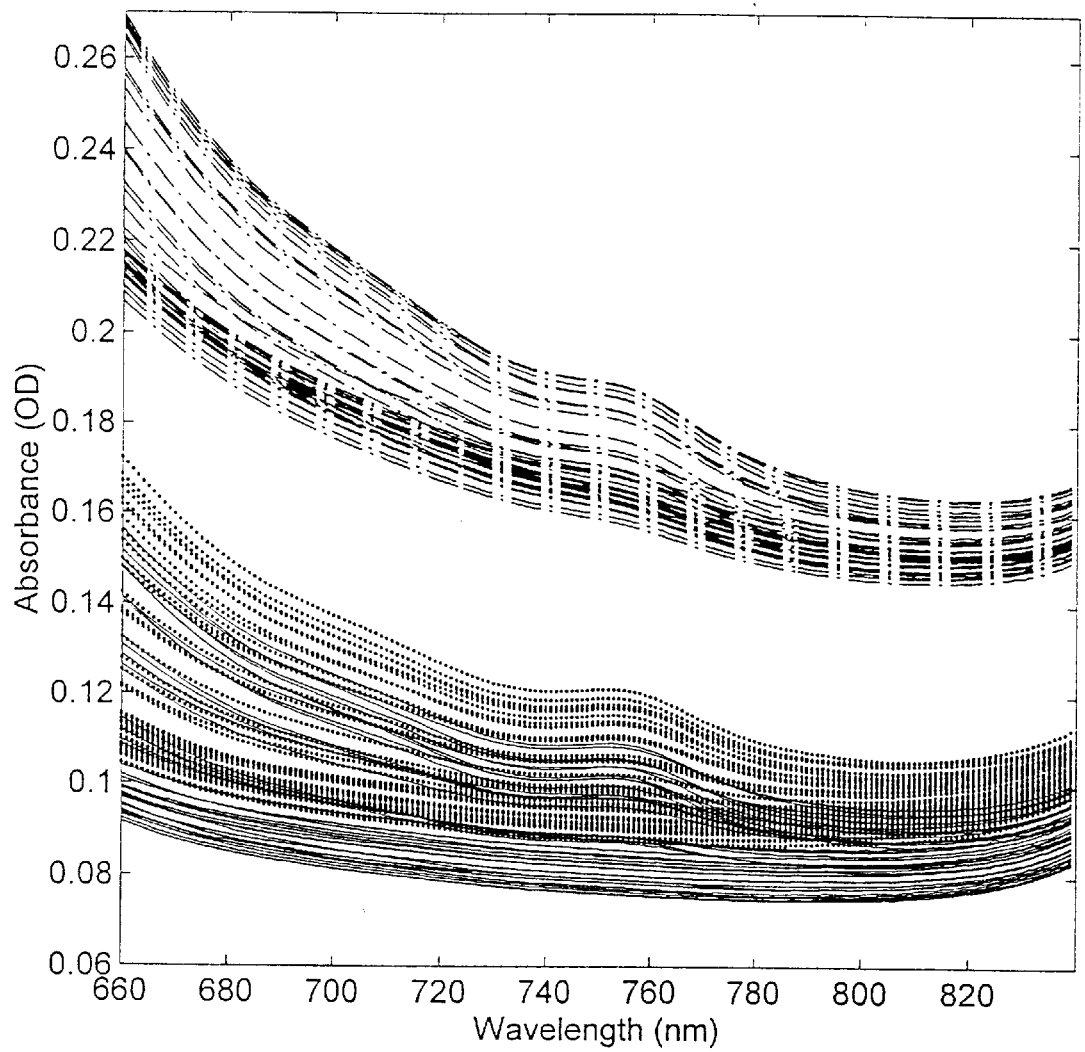
FIG. 9 is a graph of the unprocessed near-infrared absorption spectra for the in vitro validation of the partial least squares analysis using transmission through two cuvettes. The set of spectra depicted by the solid lines are from the spectra obtained from light passing through the myoglobin-containing cuvette and a blank. The spectra shown as dotted lines are from light traversing the myoglobin cuvette and the oxyhemoglobin cuvette. The dashed lines correspond to spectra from the myoglobin and deoxymyoglobin cuvettes.

Calibration of the partial least squares method was performed using the transmission spectra obtained in the two cuvette configuration. The spectra obtained included three related sets of data. The raw absorbance spectra are shown in FIG. 9. The sets of spectra with greater absorbance are from combined myoglobin and hemoglobin, including both deoxyhemoglobin (dashed line) and oxyhemoglobin (dotted line). The lower set in the figure (solid line) is from the pure myoglobin solution. The changing baseline is due to the differences in scattering from the presence of *E. coli*.

Figure 10:
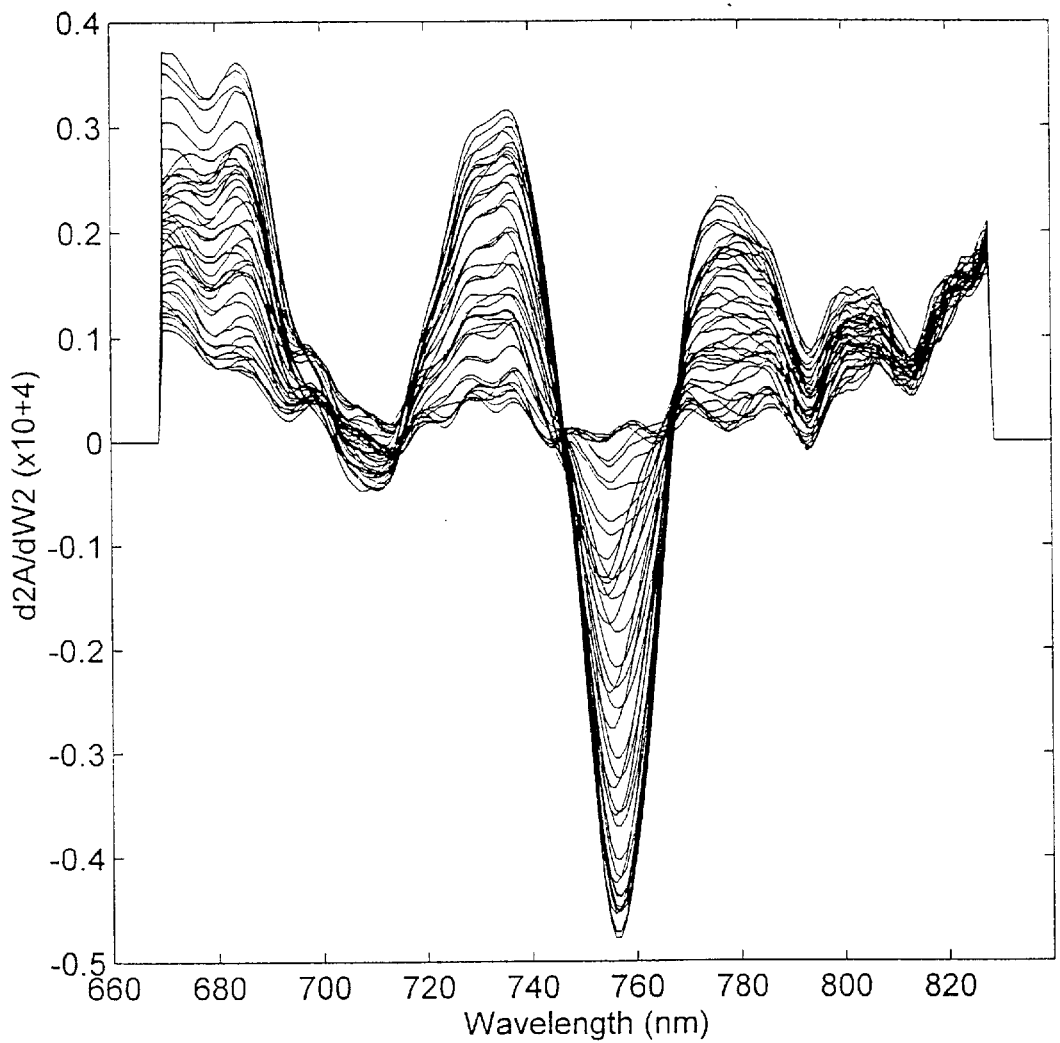
FIG. 10 illustrates second derivative spectra from the data set shown in FIG. 9. The difference between the oxygenated and deoxygenated spectra become more pronounced. The most oxygenated spectra are the flattest spectra. The deep negative peak around 756 nm is a result of the presence of either deoxyhemoglobin or deoxymyoglobin. The leftward shift of some of these peaks due to deoxyhemoglobin can be seen.

In order to remove baseline off-sets from the raw absorption spectra, second derivatives of the spectra were calculated. Discrete derivatives were determined using a second difference method, with a 3 pixel window and a 7 pixel gap (Arakaki, L. S. L. and Burns, D. H. (1992), "Multispectral analysis for quantitative measurements of myoglobin oxygen fractional saturation in the presence of hemoglobin interference," Appl. Spectrosc. 46:1919–1927). The derivative spectra were analyzed by the partial least squares method, using an algorithm written in the Matlab programming language (The Math Works, Natick, Mass.). FIG. 10 shows the second derivatives for the calibration data set using the near-infrared spectral region. The subtle difference between the oxygenated an deoxygenated spectra seen in FIG. 9 becomes pronounced in the second derivative spectra. The presence of hemoglobin in a subset of the spectra can be seen by the left-ward shift of some of the negative peaks near 760 nm.

From the myoglobin solution without hemoglobin, fractional oxygen saturations were determined for the visible region (500–650 nm) using the method previously described by Arakaki and Burns (Arakaki, L. S. L. and Burns, D. H. (1992), "Multispectral analysis for quantitative measurements of myoglobin oxygen fractional saturation in the presence of hemoglobin interference," Appl. Spectrosc. 46:1919–1927). Since the change in oxygenation of the *E. coli* and myoglobin solution was time dependent and the time of each spectral acquisition was recorded, saturations for the combined myoglobin and hemoglobin spectra were calculated by linear interpolation from the values determined from the myoglobin solution alone. The change in myoglobin oxygen saturation (data not shown) of the solution follows a smooth sigmoid shaped curve as expected.

The three sets of spectra with corresponding saturations were separated into a calibration data set and a prediction data set. These two sets of spectra included myoglobin spectra with and without hemoglobin interference. The spectra were then analyzed independently by the partial least squares method, using the near-infrared region from 660 to 840 nm.

From the calibration data set, partial least squares regression determined the eigenvectors, or factors, which best described the variation in the data that correspond to the known saturations. Using these factors, the spectra in the data set were reconstructed, and the difference between the original reconstructed spectra were used to determine the error in the prediction. Inclusion of more factors will decrease the error in prediction, however overfitting the data results in the inclusion of extra noise in the system, so that restricting the analysis to a smaller number of factors leads to a stronger predictive value (Haaland, D. M. and Thomas, E. V. (1988) Anal. Chem. 60:1193–1202).

The error in prediction can be determined as the difference between the original spectra and the reconstructed spectra. In a test of the calibration set against itself, it would be expected that the best fit would occur when all of the factors are used. In a comparison of a calibration set to an unknown data set, the addition of more factors after a certain number serves only to describe more noise in the system, and thus the error will begin to increase.

Theoretically there are four major contributors to the in vitro spectral information non-scattering media. These are the oxygenated and deoxygenated forms of hemoglobin and myoglobin. A fifth contributor may be the small amount of scattering due to the *E. coli* in solution. The contribution from other absorbing species should be roughly an order of magnitude less. Thus it is not surprising that the relative error is reduced with the inclusion of 5 factors, but inclusion of additional factors has little effect on further reduction of the predicted error.

Using these 5 factors, a set of calibration coefficients were determined that when combined with the original (second derivative) spectrum, resulted in the saturation value. Using the calibration coefficients determined from the first half of the data set, the saturation values for the other half of the data were predicted. These values were plotted against the saturation values determined from the visible spectral region (not shown) showing a good linear fit (SEE=0.003, and $R2=0.999$) which demonstrates that the myoglobin saturation can be predicted from the near-infrared spectra which contain either oxyhemoglobin or deoxyhemoglobin interference.

The solutions needed for the in vitro development of a useful calibration set must produce spectra which yield the same kind of information which would be found in reflectance spectra from a beating blood perfused heart. The major absorbing species in this tissue are hemoglobin and myoglobin. Other absorbing species, including the cytochromes, are present in significantly lower concentration (Drabkin, D. (1950), "The distribution of the chromoproteins, hemoglobin, myoglobin, and cytochrome c, in the tissues of different species, and the relationship of the total content of each chromoprotein to body mass," J. Biol. Chem. 182:317–333), such that their effect on the spectra is less than 10% and could be ignored. In addition to absorbance, light transmission in tissue is significantly attenuated by scattering. Thus, the calibration set must include spectra with a range of concentrations of four absorbing species; oxyhemoglobin, deoxyhemoglobin, oxymyoglobin, and deoxymyoglobin, and a range of levels of scattering (Arakaki, L. S. L. and Burns, D. H. (1992), "Multispectral analysis for quantitative measurements of myoglobin oxygen fractional saturation in the presence of hemoglobin interference," Appl. Spectrosc. 46:1919–1927).

These five variables must be allowed to vary independently of one another. In tissue, the oxygen saturation of hemoglobin and myoglobin may be quite different at any given time, since hemoglobin is present in the red blood cells circulating in the vasculature, and myoglobin is found within the myocytes. The calibration set was developed by the mathematical addition of the raw spectra obtained from individual solutions of hemoglobin and myoglobin in scattering media.

Concentrations of hemoglobin used were determined to cover the range expected to be found in cardiac tissue. Cardiac tissue has approximately 5% blood by volume under normal working conditions (Feigl, E. O. (1983), "Coronary Physiology," Physiol Rev. 63:1–205). To cover a wider possible range, the final calibration set included blood concentrations of 2.5%, 5% and 10% using blood with a hematocrit of 45%. Myoglobin solutions were made up with a fmal concentration of 100 $\mu$M, as a review of the literature gives reported values for dog cardiac myoglobin concentrations from 80 to 120 $\mu$M (Meng, H. et al. (1993), "Myoglobin content of hamster skeletal muscle," J. Appl. Physiol. 74:2194–2197; Kagan, L. (1973), "Myoglobin: Biochemical, Physiological, and Clinical Aspects," New York, Columbia University Press, pp. 9–13).

To simulate tissue conditions light scattering was produced by the addition of homogenized dairy cream half & half. Synthetic creamers and dairy cream half & half have been shown to reliably produce scattering conditions which closely mimic tissue Arakaki, L. S. L. and Burns, D. H. (1992), "Multispectral analysis for quantitative measurements of myoglobin oxygen fractional saturation in the presence of hemoglobin interference," Appl. Spectrosc. 46:1919–1927; Marble, D. M. et al. (1994), "Diffusion-based model of pulse oximetry: in vitro and in vivo comparison," Appl. Opt. 33(7):1279–1285). However, rapid oxidation of myoglobin to metmyoglobin in non-dairy creamer prohibited its use. Five scattering levels were chosen for the final calibration set ranging from 10–40% dairy cream half & half.

Solutions of myoglobin and hemoglobin were respectively made up to represent each of the conditions listed above. Multiple spectra were obtained from each solution using the reflectance probe after the solutions were well oxygenated by gentle bubbling with 100% oxygen. The solutions were continuously stirred during the data collection to prevent any settling of the components. Following the acquisition of each set of oxygenated spectra, excess dithionite was added to each solution. After sufficient time for complete reduction, multiple spectra of the deoxygenated samples were collected.

From the 1220 experimentally obtained spectra, oxygenated and deoxygenated hemoglobin and myoglobin spectra were mathematically added to produce a range of new spectra representing 5 scattering levels, 3 hemoglobin concentrations, 5 hemoglobin saturations, and 11 myoglobin saturations. A total of 825 spectra were developed in this manner. Scattering level was kept the same for hemoglobin and myoglobin spectra for any given addition. At least 5 spectra were obtained for each condition, and to prevent the propagation of non-random noise throughout the calibration set, spectra from each of these subsets were randomly added to other random spectra from another given subset, using a random number generator function. Spectral additions and processing were carried out using the matrix software program Matlab (The Math Works, Natik, Mass.).

Four adult mongrel male dogs were used in this study. The animals were premedicated with morphine (3 mg.kg sc) and anesthetized with α-chloralose (100 mg/kg), intubated and ventilated mechanically with a pressure controlled ventilator (Harvard Apparatus Model #708). Cannulas were placed in the left and right femoral veins and arteries, and arterial blood pressure was continually monitored. End-tidal $CO_2$ (Beckman Medical Gas Analyzer LB-2) and arterial blood gasses were measured (Instrumentation Laboratory 1306) to maintain $pCO_2$ between 35 and 45 torr, and $PO_2$ between 100 and 140. Intravenous sodium bicarbonate was administered as necessary to maintain the pH between 7.34 and 7.40.

A median sternotomy was performed, and a pericardial cradle was created to expose the left ventricular surface. A pacing electrode was stitched to the right atrium. Anticoagulation with heparin was begun, and the left main coronary artery was cannulated and perfused with blood from the left femoral artery at a constant pressure measured at the cannula tip using a servo controlled pump (Mohrman, D. E. and Feigl, E. O. (1978), "Competition between sympathetic vasoconstriction and metabolic vasodilation in the canine coronary circulation," Circ. Res. 42:79–86). A coronary occlusion snare was made by placement of a loose ligature around the distal left anterior descending coronary artery.

The optical probe was positioned above the left ventricular surface, over an avascular region between the left anterior descending artery and one of its diagonal branches on the left ventricle, distal to the placement of the occluding snare. The height of the probe was adjusted so that at maximal lung inflation the myocardial surface just contacted the probe.

To reduce motion artifact, spectral acquisition was gated to both the cardiac and respiratory cycles with an exposure time of 100 ms. This was accomplished using the ventilator cycle as a master-clock, which in turn triggered the stimulator for pacing the heart. A fiduciary delay allowed for accurate timing of the spectral acquisition during late diastole and during the peak inspiratory plateau of the respiratory cycle. Thus data were obtained from one cardiac cycle per respiratory cycle. The illuminating light source shutter opened only during data acquisition, to minimize heating of the tissue. Data acquisition controlling software was written in Microsoft C/C++ (Microsoft, Redmond, Wash.).

To account for small changes in the optical configuration between experiments, calibration of the photo diode array was performed using spectral intensity lines at 546.1 nm and 809.4 nm from a mercury lamp. In addition, an absorption peak at 830 nm which was noted to be constant for each data set as well as in the calibration set was used as an internal standard. This absorption peak is probably due to CH groups present in both the calibration solutions and the in vivo tissue.

Second difference processing with regard to wavelength was used to remove baseline offsets from the data sets (Arakaki, L. S. L. and Burns, D. H. (1992), "Multispectral analysis for quantitative measurements of myoglobin oxygen fractional saturation in the presence of hemoglobin interference," Appl. Spectrosc. 46:1919–1927), and the wavelength region from 660 to 840 nm was used for the analyses. The calibration coefficients determined from the calibration set described above were then multiplied at each corresponding wavelength. The sum of these multiples results in a relative saturation value. These values were then scaled within each data set, using the mean value for spectra acquired with 100% oxygen and adenosine as the maximal saturation value. Similarly, the mean value for the spectra from the coronary occlusion on room air was used as the lowest saturation value. All values were then scaled to these extremes, and are reported as relative saturation, in percent. The conditions studied were as follows:

Maximal myoglobin oxygen saturation was achieved by ventilation with 100% oxygen, and simultaneous intracoronary infusion of adenosine. Adenosine is a potent coronary vasodilator (Feigl, E. O. (1983), "Coronary Physiology," Physiol. Rev. 63:1–205). Adenosine infusions were started at 0.5 cc/min of a 1 mM solution, and increased to 1.0 cc/min. If no further increase in coronary flow was noted, the infusion was returned to 0.5 cc/min.

Minimal myoglobin oxygen saturation was produced by creating an ischemic area of myocardial tissue while ventilating the animal with room air. Ischemia was produced by occluding the left anterior coronary artery with a snare. The occlusion was maintained for either 60 or 90 seconds and then released. Spectra were acquired for at least 5 minutes following release of the occlusion.

Continuous spectra were acquired at the start of each experiment after the probe was appropriately positioned over the area of myocardium of interest. Timing of the spectral acquisition was verified by simultaneous recording of the respiratory pressure, the left ventricular pressure, and the start of spectral acquisition. Baseline spectra were also collected between each experimental change.

For each animal studied, spectra were acquired continuously while the animal was breathing room air through the ventilator circuit. After establishing a baseline, the ventilator intake was connected to a 100% oxygen source.

"Fluosol" (TRADEMARK) is a perflurocarbon with a high oxygen solubility which was developed for use an intravascular blood substitute for intracoronary perfusion during angioplasty (Cleman, M. et al. (1986), "Prevention of ischemia during percutaneous transluminal coronary angioplasty by transcatheter infusion of oxygenated "Fluosol" DA 20%," Circulation 74:555–562). Because of its high oxygen solubility, it is an ideal agent to replace the blood perfusion in the coronary artery, while maintaining adequate oxygen delivery. Two parallel servo controlled pumps were used to alternately provide for blood perfusion (as described earlier) or for "Fluosol" perfusion. The servo control allowed for maintenance of a constant coronary infusion pressure by changes in the flow rate. "Fluosol" perfusion was performed in 3 of 4 experimental animals. In two of the four animals a coronary occlusion was performed while the coronary was perfused with "Fluosol".

Having demonstrated that the partial least squares method can reliably predict myoglobin oxygen saturation in the presence of hemoglobin from the near-infrared spectral region, development of a calibration set using scattering solutions was needed to provide calibration coefficients to interpret the in vivo data. Partial least squares analysis was performed with 825 calibration spectra including scattering agent using the wavelength region from 660 to 840 nm.

Figure 11:
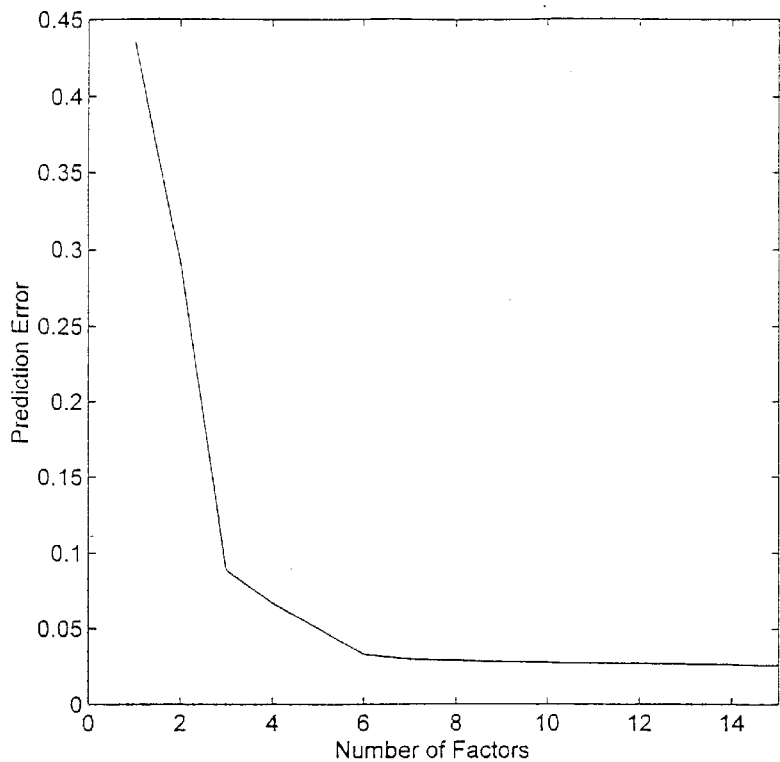
FIG. 11 is a graph of prediction error for the calibration set developed from the reflectance spectra in scattering media as a function of the number of factors included in the set. The use of five factors (eigenvectors) reduces the prediction error to 0.05. Although inclusion of more factors may decrease the prediction error further in this particular test of the calibration set against itself, use of too many factors to describe the in vivo data will result in inclusion of excessive amounts of noise.

As discussed above, the optimal number of factors to include in determining the calibration coefficients can be determined by examining the prediction error. A plot of the 'PRedicted Error Sum of Squares' or 'PRESS set' can be used to illustrate the decrease in error as more factors are used to predict the spectra (FIG. 11). As the number of factors increases, the error decreases to a minimum value.

Figure 12:
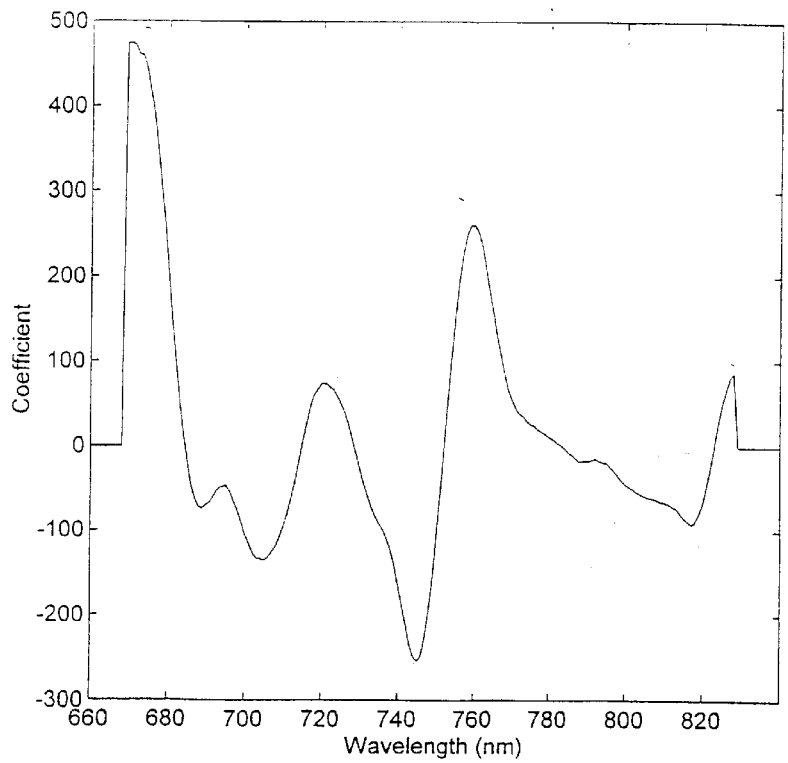
FIG. 12 shows the calibration coefficients for the calibration set from the reflectance experiments in scattering media in the near-infrared region. Positive correlation with oxygenated myoglobin is greatest around 720 to 760 nm. In addition there is strong positive correlation for wavelengths at the tail-end of the visible spectrum.

Using 5 factors from the partial least squares analysis, the saturations for each spectrum can be predicted by a set of calibration coefficients. The set of calibration coefficients forms a spectrum of values for each wavelength utilized in the analysis. The calibration coefficients determined in this manner are shown in FIG. 12. The first and last eleven wavelengths are excluded from the analysis due to the smoothing routine in the second derivative algorithm. The dot product of these coefficients with any second derivative spectrum in this wavelength region yields an estimate of the associated saturation value.

The calibration coefficients can then be used to predict the original saturation to determine how well the calibration set can predict itself. The mean predicted values (+/−I standard deviation) for the 825 spectra in the calibration set were plotted against the known saturation values (not shown). The standard deviation of the predicted values from the known saturations is 2.0%. This suggests that the calibration set readily predicted itself with a high degree of accuracy.

Having demonstrated that the calibration set can reliably predict itself, the next step is to demonstrate that the calibration spectra are sufficiently similar to the in vivo data set. The overlap of the calibration spectra with the experimental data sets visibly appears quite good. Two statistical methods were applied to these two spectral sets to quantitatively evaluate this. The Mahalanobis distance test (Whitfield, R. G. et al. (1987) Appl. Spectrosc. 41:1204–121) has been used for comparing, two spectral data sets by calculating a single value for a given spectrum. In this case the factors are determined by the partial least squares method. Graphically this can best be represented by demonstration of the Mahalanobis distance (M-distance) in a 2 dimensional plane. However, the actual distance is calculated by using all of the factors selected. A total of 586 spectra from oxygenated and deoxygenated blood and "Fluosol"-perfused heart were included from the animal studies for comparison with the calibration set. All of the spectra used in the subsequent analyses were included in this test set of in vivo spectra. The M-distances for each of these in vivo spectra were calculated and for all 586 spectra, the M-distances were calculated as falling within the three standard deviations from the mean center of mass. Since the purpose of the M-test is to compare two spectral data sets for similarity, a good fit should demonstrate overlap to 3 standard deviations. For example, calculating M-distances for a single data set against itself will result in 95% of the data falling within three standard deviations of the center of mass. A two-dimensional projection of the Mahalanobis distances for the calibration set and M-distances for the in vivo spectra were superimposed on a plot (data not shown). All of the in vivo spectra were within three standard deviations from the mean of the calibration set. Thus, the results of this M-test supports the assumption that the experimental data are well represented by the calibration set.

An alternative approach to validating the calibration set is by calculating the relative residual error, or residual ratio (RR) (Aldridge, P. K. (1994), "Identification of tablet formulations inside blister packages by near-infrared spectroscopy," Appl. Spectros. 48:1272–1276). A residual ratio of less than 50 has been used to demonstrate similarity between two data sets. A comparison of the 586 in vivo spectra to the 825 calibration spectra yields a residual ratio value of 8.9 indicating good similarity between the two data sets.

Baseline myoglobin saturation values were determined for all four animals. Using oxygen and adenosine as the maximal saturation (i.e. 100% saturation) and the occlusion saturation as zero, the baseline saturations ranged from 81 to 94%, as shown in Table 3. The average value from these experiments was 89%. Administration of 100% oxygen via the ventilator made a small but significant increase in the saturation value. In the 4 animals in which this was studied, there was an increase in saturation of 5.2% from the pre oxygen (room air) baseline. FIG. 13 shows the increase with oxygen administration. Occlusion of a branch coronary artery resulted in reproducible myoglobin oxygen desaturation. The desaturation was prompt, and within 30 seconds reached a minimum which was maintained fairly evenly until release of the occlusion. On reperfusion there was an equally prompt increase in saturation value to somewhat above baseline. This overshoot returned toward baseline within 30 seconds. The mean increase during reperfusion was 9% over baseline. The average peak reperfusion saturation was 98%, as shown in Table 3. FIG. 13 shows a result from a coronary occlusion experiment.

In order to demonstrate insensitivity of the analysis to hemoglobin, coronary perfusion was changed from oxygenated blood to oxygenated "Fluosol" in 3 animals. Intracoronary infusion of adenosine was maintained during the transition from blood to "Fluosol" to insure maximal coronary perfusion. In 2 of the 4 animals, coronary occlusion was performed by coronary snare while on fluosol. Mean saturation values for the oxygenated fluosol perfused heart and saturation values during coronary occlusion while on "Fluosol" are shown in Table 3. The mean value for the 3 animals was 93.6% saturation with oxygenated "Fluosol", and 6.4% saturation during the occlusions.

FIG. 14 shows raw reflectance spectra from the heart under oxygenated and deoxygenated conditions, with "Fluosol" or blood perfusion. The absolute magnitude of the absorbance is notably higher for the oxy and deoxy spectra with blood perfusion. Although not readily apparent from this figure, there is a slight rightward shift of the deoxy peak in the "Fluosol" perfused spectrum due to the absence of hemoglobin, as expected.

In addition to the experimental test with "Fluosol" described above, the effect of hemoglobin on the sensitivity of the analysis was also investigated by mathematical addition of hemoglobin spectra to the in vivo data set. Sets of spectra were obtained from each animal studied which included oxygenated myocardium with blood perfusion and oxygenated myocardium with "Fluosol" perfusion. Also, sets of spectra were obtained from three animals which included deoxygenated myocardium with either blood perfusion or "Fluosol" perfusion. Difference spectra were then determined using wavelength by wavelength subtraction of the spectra from "Fluosol" perfused myocardium from the blood perfused myocardium. This resulted in spectra which contained the component of the in vivo reflectance spectra determined primarily by hemoglobin in either the oxygenated or deoxygenated state. Other tissue spectral characteristics, including myoglobin, were thus subtracted out.

These difference spectra were then added back to the entire in vivo data set from each respective animal to mathematically double the hemoglobin content in each spectrum (first oxygenated then deoxygenated). The myoglobin oxygen saturation was recalculated for these new spectra containing roughly double the hemoglobin concentration. The difference in myoglobin saturation for each spectrum was then determined.

The mean difference in myoglobin saturation calculated by doubling the hemoglobin concentration with either oxygenated or deoxygenated hemoglobin was 9.8%. The change in myoglobin saturation determined by adding only deoxygenated hemoglobin spectra to the in vivo spectra was 14.1%, while that for oxygenated hemoglobin was 6.0%. Addition of less hemoglobin resulted in proportionately less difference in myoglobin saturation. These results suggest that the overall sensitivity of the myoglobin saturation determination to changes in hemoglobin concentration is on the order of 10% of the hemoglobin concentration. In other words, an increase in hemoglobin concentration in the myocardium of 50% would result in approximately a 5% error in the myoglobin saturation determination by this method.

These experiments demonstrate that myoglobin oxygen saturation can be determined in the presence of hemoglobin using near-infrared reflectance spectroscopy and partial least squares analysis. The in vitro experiments with separate cuvettes containing myoglobin and hemoglobin at different saturations validate the spectroscopic methods. The in vivo experiments described herein indicate that myoglobin oxygen saturation can be determined using the methods of this invention in a blood-perfused, beating heart, using an in vitro calibration set developed from hemoglobin and myoglobin in scattering media.

The use of an in vitro calibration set to accurately interpret in vivo data is predicated upon the assumption that the in vitro and in vivo data sets are sufficiently similar. The results herein demonstrate using two generally accepted comparative methods (the Mahalanobis distance test and the residual ratio test) to compare these spectral data sets that the calibration set used to interpret the in vivo data closely represent the variation seen in the experimental data set. These tests validate the use of calibration sets developed as described herein for in vivo determinations of myoglobin oxygen saturation and intracellular oxygen tension.

The partial least squares analysis yields relative saturation values These values are useful in providing information about relative myoglobin oxygen saturation and intracellular oxygen tension. For example, relative saturation values can be used to follow changes in tissue oxygenation over time, for example during medical procedures. Absolute saturation values can be derived from the relative values using a scaling method. Scaling of the relative data can be done using physiologic endpoints chosen to give extreme upper and lower myoglobin saturation values. However, the myoglobin saturation at the lowest endpoint (coronary occlusion) is probably not quite zero. Although it may be assumed that mitochondrial function will continue at least until the cytochrome oxidase system is half saturated ($pO_2$ of less than 0.5 forr) (Wittenberg, B. and Winnenberg, J. B. (1989), "Transport of oxygen in muscle," Annu. Rev. Physiol. S1:857–878), myoglobin may not be completely desaturated when the flow of oxygen is halted. To the extent that coronary occlusion does not decrease cellular oxygen tension to zero, the percent labile signal reported in Table I will be lower than the true myoglobin oxygen saturation. The myoglobin saturation upper endpoint may also be inaccurate if the myoglobin is less than fully saturated with 100% oxygen and vasodilatation with adenosine. As described by the Hill equation, fully saturated myoglobin can only occur with 100% oxygen at an infinite $pO_2$ (Schenkman, K. A. et al. (1997), "Myoglobin oxygen dissociation by multiwavelength spectroscopy," J. Appl. Physiol.). In addition, the flux of oxygen through the cell due to mitochondrial respiration may preclude complete myoglobin oxygen saturation. To the extent that coronary perfusion during maximal adenosine vasodilation and 100% oxygen breathing does not completely saturate myoglobin, the percent labile signal reported in Table 3 will be higher than the true myoglobin oxygen saturation.

Example 3

Myoglobin Dissociation Curves

Two methods were employed to determine myoglobin dissociation curves to allow determination of p50 values under physiological conditions and ultimately to determine intracellular oxygen tension from myoglobin saturation data.

Method 1: Reflectance spectra were acquired from solutions containing 50 $\mu$M myoglobin, 50% volume scatterer, 400 $\mu$L E. coli, and 50 mM phosphate buffer at pH 7.6. The total volume was 1.75 mL. Three data sets within each of two temperature ranges, 23.0°C.±0.1° C. and 26.1° C.±0.3, were collected. In each trial, the full range of myoglobin fractional saturation values was sampled. During spectral acquisitions, $pO_2$ readings from the oxygen electrode and temperatures from a Chromel/Alumel thermocouple (John Fluke Mfg. Co., Inc., Everett, Wash.) were recorded. Both the electrode and thermocouple were inserted into the myoglobin solution at the same vertical level in the cuvette as the center of the fiber bundle. Care was taken to keep them 2 mm away from the optical probe so that they did not interfere with the optical measurement. All solutions were mixed with a magnetic stir bar and plate. A classical least squares (CLS) analysis was used to determine the fractional saturation for each of these spectra (Arakaki, L. S. L. and Burns, D. H. (1992) Appl. Spectrosc. 46:1919; Haaland, D. M. and Thomas, E. V. (1988) Anal. Chem. 60:1193). The CLS algorithm assumed that myoglobin spectra were linear combinations of pure oxymyoglobin and deoxymyoglobin spectra, and determined the fractional contribution of each. Eq. 1 was then used to compute myoglobin fractional saturation. CLS coefficients and the basis myoglobin spectra represented the measured spectra accurately. Residuals between the original spectra and the dot product of CLS coefficients with the basis spectra were on the same order of magnitude as the spectral noise.

Myoglobin oxygen dissociation curves were constructed at each temperature by plotting $pO_2$ measurements against the corresponding fractional saturation values from CLS analysis. Values for p50 were calculated at each temperature from these data using Hill plots.

Hill plots ($\log(S/1(1-S))$ vs. $\log(pO_2)$) were constructed for data at 23.0° C. and 26.1° C. (data not shown). The theoretical value for the slope of the Hill plot is 1 because myoglobin has a single binding site and does not display cooperative binding with other molecules. Linear regressions identified the best lines through the points of each of the three data sets at each temperature. At 23.0° C., the slope of the best-fit line was 1.16±0.26, and at 26.1° C., the slope was 1.21±0.40. Values for p50 were obtained from the log of the y-intercept of the Hill plot. The p50 value was 0.56±0.27 Torr at 23.0° C. and 0.75±0.24 Torr at 26.1° C. These numbers are lower than other published values for horse heart myoglobin. In these studies, p50 values of approximately 1 Torr are reported for temperatures of 20–23° C. (Oshino, R. et al. (1972) Biophys. Acta 273:5; Tamura, M. et al. (1973) Biochim. Biophys. Acta 317:34; Ross, P. D. and Warme, P. K. (1977) Biochemistry 16:2560). Differences in the values obtained by this method may be due to inaccuracies in oxygen electrode measurements at very low $pO_2$ values.

Method 2: Myoglobin oxygen dissociation was determined by multiwavelength spectroscopy substantially as described in K. A. Schemkman et al. (1997) J. Appl. Physiol. 82(1):86–91 (January 1997), which methodology is incorporated in its entirety by reference herein. This method analyzes myoglobin-$O_2$ binding using 150 wavelengths (500–650 nm) while simultaneously measuring and correcting for metmyoglobin contamination that is encountered in vitro. The myoglobin-$O_2$ curves were determined with 16 gas mixtures of known $O_2$ fraction, plus a zero point obtained with sodium dithionite. Measurements were made at several temperatures (10–40° C.) and at pH values between 6.5–7.5.

All publications referred to herein are hereby incorporated by reference. Although the invention is described with respect to specific embodiments herein, equivalent means are known to the art for performing various steps, and the invention encompasses all such means.

TABLE I

Results of computer simulations

| Characteristic of prediction set | [hemoglobin]: [myoglobin] ratio | Volume of Scatterer (%) | Optimal # of factors | SE | $R^2$ |
|---|---|---|---|---|---|
| median values of calibration set | 2:1 | 50 | 3 | 0.017 | 0.999 |
| increase in myoglobin content | 2:2 | 50 | 3 | 0.010 | 0.999 |
| decrease in myoglobin content | 2:0.5 | 50 | 3 | 0.019 | 0.998 |
| increase in hemoglobin concentration | 3:1 | 50 | 3 | 0.021 | 0.998 |
| decrease in hemoglobin concentration | 1:1 | 50 | 3 | 0.008 | 0.999 |
| increase in scattering level | 2:1 | 50 | 3 | 0.016 | 0.999 |
| decrease in scattering level | 2:1 | 50 | 3 | 0.053 | 0.991 |

TABLE II

Results of in vitro experiments.

| Physiological state simulated by prediction set: | [myoglobin] ($\mu$M) | [hemoglobin] ($\mu$M) | Volume of scatterer (%) | # Spectra in prediction set | Optimal # of factors | SE | $R^2$ | % Spectra classified as outliers |
|---|---|---|---|---|---|---|---|---|
| moderate increase in blood volume | 50 | 150 | 55 | 32 | 2 | 0.067 | 0.948 | 0 |
| large increase in blood volume | 50 | 200 | 60 | 36 | 2 | 0.060 | 0.965 | 0 |
| increase in scattering level | 50 | 100 | 75 | 35 | 2 | 0.082 | 0.931 | 0 |
| decrease in scattering level | 50 | 100 | 25 | 40 | 2 | 0.035 | 0.986 | 0 |
| increase in myoglobin content | 75 | 100 | 50 | 22 | 3 | 0.027 | 0.991 | 0 |
| decrease in myoglobin content | 25 | 100 | 50 | 23 | 3 | 0.037 | 0.983 | 0 |

Table 3: Same as in Schenkman Manuscript

TABLE III

Cardiac myoglobin oxygen saturation in percent of labile signal from in vivo experiments.

|  | Dog 1 | Dog 2 | Dog 3 | Dog 4 | Mean |
|---|---|---|---|---|---|
| Oxygen and adenosine | 100 | 100 | 100 | 100 | 100 |
| Coronary occlusion | 0 | 0 | 0 | 0 | 0 |
| Room-air baseline | 94.3 | 89.5 | 91.3 | 81.0 | 89.0 |
| Peak reperfusion | 107.4* | 94.3 | 98.1 | 91.9 | 97.9 |
| Oxygen | 98.8 | 95.3 | 94.8 | 87.8 | 94.2 |
| "Fluosol", oxygen and adenosine | — | 103.3* | 86.3 | 91.1 | 93.6 |
| "Fluosol" with occlusion | — | 13.2 | — | −0.5* | 6.4 |

Percent saturation determined from the reflectance spectra, using the values for the reflectance spectra from oxygen and adenosine administration as the maximum labile signal, and the values for blood perfused coronary occlusions as the minimum signal.
*denotes calculated values above 100% or below 0%.

We claim:

1. A method for determining myoglobin fractional oxygen saturation in vivo in muscle tissue which comprises the steps of:
   (a) measuring an absorption spectrum of a muscle tissue in vivo,
   (b) calculating the myoglobin fractional oxygen saturation of said tissue from said measured absorption spectrum using calibration coefficients determined from multivariate analysis employing a calibration set comprising in vitro absorbance spectra wherein in the spectra of said calibration set myoglobin and hemoglobin saturation are varied independently of one another.

2. The method of claim 1 wherein in step (a) a derivative of said spectrum is taken prior to step (b) and wherein in step (b) said calibration set comprises derivatives of said in vitro absorbance spectra.

3. The method of claim 1 wherein in step (a) second-derivative of said spectrum is taken prior to step (b) and wherein in step (b) said calibration set comprises second-derivatives of said in vitro absorbance spectra.

4. The method of claim 1 wherein said muscle tissue is blood-perfused muscle tissue.

5. The method of claim 1 wherein said absorption spectrum is measured in the visible or near-infrared wavelength region.

6. The method of claim 1 wherein said absorption spectrum is measured using diffuse reflectance spectroscopy.

7. The method of claim 6 wherein said absorption spectrum is measured in the near-infrared wavelength region.

8. The method of claim 6 wherein said absorption spectrum is measured in the visible wavelength region.

9. The method of claim 6 wherein a reflectance spectrum is obtained employing a fiber optic contact probe comprising spatially separated illuminating and detection fibers.

10. The method of claim 9 wherein the minimal spacing between the illuminating and detection fibers in said fiber optic probe is between about 1 mm to about 3 mm.

11. The method of claim 1 wherein said multivariate analysis is a partial least squares analysis.

12. The method of claim 1 wherein a scattering agent is represented in spectra of said calibration set.

13. A method for determining intracellular oxygen tension in vivo in muscle tissue which comprises the steps of:
   (a) determining the myoglobin fractional oxygen saturation of said muscle tissue in vivo by:
      (i) measuring an absorption spectrum of a muscle tissue in vivo, and taking a derivative of said spectrum;
      (ii) calculating the myoglobin fractional oxygen saturation of said tissue from said measured absorption spectrum using calibration coefficients determined from multivariate analysis employing a calibration set comprising derivatives in vitro absorbance spectra wherein in the spectra of said calibration set myoglobin and hemoglobin saturation are varied independently of one another; and
   (b) calculating the intracellular oxygen tension of said muscle tissue from the oxygen saturation data of step(a) employing a p50 value obtained from an optical spectroscopic determination of myoglobin-oxygen dissociation curves.

14. The method of claim 13 wherein in step (a) a derivative of said spectrum is taken prior to step (b) and wherein in step (b) said calibration set comprises derivatives of said in vitro absorbance spectra.

15. The method of claim 13 wherein in step (a) second-derivative of said spectrum is taken prior to step (b) and wherein in step (b) said calibration set comprises second-derivatives of said in vitro absorbance spectra.

16. The method of claim 13 wherein said myoglobin-oxygen dissociation curves are determined using multiwavelength spectroscopic analysis.

17. The method of claim 16 wherein said myoglobin-oxygen dissociation curves are determined by a method which compensates for the presence of metmyoglobin.

18. The method of claim 13, wherein said muscle tissue is blood-perfused muscle tissue.

19. The method of claim 13 wherein said absorption spectrum is measured in the visible or near-infrared wavelength region.

20. The method of claim 13 wherein said absorption spectrum is measured using diffuse reflectance spectroscopy.

21. The method of claim 20 wherein said absorption spectrum is measured in the near-infrared wavelength region.

22. The method of claim 20 wherein said absorption spectrum is measured in the visible wavelength region.

23. The method of claim 13 wherein said multivariate analysis is a partial least squares analysis.

24. The method of claim 13 wherein a scattering agent is represented in spectra of said calibration set.

* * * * *

UNITED STATES PATENT AND TRADEMARK OFFICE
CERTIFICATE OF CORRECTION

PATENT NO. : 5,931,779

DATED : Aug. 3, 1999

INVENTOR(S) : Arakaki et al.

It is certified that error appears in the above-identified patent and that said Letters Patent is hereby corrected as shown below:

On the cover page of the patent, column 1, under "[75] Inventors:" please replace "Kenneth H." with --Kenneth A.--

At column 5, line 62, please replace "FIG. 2" with --FIG. 2A--.

At column 5, line 66, please insert the following new paragraph before the paragraph beginning "FIG. 3A . . . " --FIG. 2B is an enlargement of the distal end of the probe of FIG. 2A.--

At column 7, line 46, please replace "FIG. 2 illustrates" with --FIGS. 2A and 2B illustrate--.

At column 7, line 62, please replace "distal end face." with --distal end face, as shown in FIG. 2B.--.

At column 8, line 63, please replace "FIG. 2 illustrates" with --] FIG. 2B illustrate--.

UNITED STATES PATENT AND TRADEMARK OFFICE
CERTIFICATE OF CORRECTION

PATENT NO. : 5,931,779

DATED : Aug. 3, 1999

INVENTOR(S) : Arakaki, et al.

It is certified that error appears in the above-identified patent and that said Letters Patent is hereby corrected as shown below:

At column 13, line 9, please rewrite "mm⁻," as --$mm^{-1}$,--.

At column 15, line 5, please rewrite "$dAd\mu_a$. is" as --$dAd\mu_a$ is--.

At column 16, line 45, please rewrite "OD/(mM mm)" as --OD/(mM•mm)--.

At column 16, line 53, please rewrite "OD/(mM m)" as --OD/(mM•m)--.

At column 18, line 23, please rewrite "fmal" as --final--.

Signed and Sealed this

Twenty-fourth Day of October, 2000

Attest:

Q. TODD DICKINSON

*Attesting Officer*     *Director of Patents and Trademarks*